(12) United States Patent
Stevenson et al.

(10) Patent No.: US 12,186,726 B2
(45) Date of Patent: Jan. 7, 2025

(54) USE OF RENEWABLE ENERGY IN THE PRODUCTION OF CHEMICALS

(71) Applicant: SABIC Global Technologies B.V., Bergen op Zoom (NL)

(72) Inventors: Scott Stevenson, Sugar Land, TX (US); Andrew Mark Ward, Redcar (GB); Tim Abbott, Redcar (GB); Kenneth Francis Lawson, Redcar (GB); Joseph William Schroer, Sugar Land, TX (US); Michael Edward Huckman, Sugar Land, TX (US); Arno Oprins, Geleen (NL); Zhun Zhao, Sugar Land, TX (US)

(73) Assignee: SABIC Global Technologies B.V., Bergen Op Zoom (NL)

( * ) Notice: Subject to any disclaimer, the term of this patent is extended or adjusted under 35 U.S.C. 154(b) by 0 days.

(21) Appl. No.: 17/310,076

(22) PCT Filed: Jan. 14, 2020

(86) PCT No.: PCT/US2020/013525
§ 371 (c)(1),
(2) Date: Jul. 15, 2021

(87) PCT Pub. No.: WO2020/150248
PCT Pub. Date: Jul. 23, 2020

(65) Prior Publication Data
US 2022/0126251 A1    Apr. 28, 2022

Related U.S. Application Data

(60) Provisional application No. 62/792,633, filed on Jan. 15, 2019, provisional application No. 62/792,627,
(Continued)

(51) Int. Cl.
*B01J 19/00* (2006.01)
*B01D 53/047* (2006.01)
(Continued)

(52) U.S. Cl.
CPC ........ *B01J 19/0053* (2013.01); *B01D 53/047* (2013.01); *B01D 53/265* (2013.01);
(Continued)

(58) Field of Classification Search
CPC .... B01J 19/08; B01J 19/0013; B01J 19/0053; B01J 19/0033; B01J 2219/00132;
(Continued)

(56) References Cited

U.S. PATENT DOCUMENTS 2,002,525 A * 5/1935 Cambron ................ C07C 5/327
422/198
3,644,100 A * 2/1972 Lhonore ................ C10G 11/04
252/373

(Continued)

FOREIGN PATENT DOCUMENTS

| CN | 85101024 | 1/1987 |
| CN | 102008972 | 4/2011 |

(Continued)

OTHER PUBLICATIONS

Anonymous: "Renewable Electrolysis Hydrogen and Fuel Cells" Oct. 2014 https://www.nrel.gov/hydrogen/renewable-electrolysis.html.
(Continued)

*Primary Examiner* — Lessanework Seifu
(74) *Attorney, Agent, or Firm* — Norton Rose Fulbright US LLP

(57) ABSTRACT

A chemical synthesis plant comprising: one or more reactors configured for producing, from one or more reactants, a process stream comprising at least one chemical product; a
(Continued)

feed preparation system configured to prepare one or more feed streams comprising one or more of the one or more reactants for introduction into the one or more reactors; and/or a product purification system configured to separate the at least one chemical product from reaction byproducts, unreacted reactants, or a combination thereof within the process stream, wherein the chemical synthesis plant is configured such that a majority of the net energy needed for heating, cooling, compressing, or a combination thereof utilized via the one or more reactors, the feed preparation system, the product purification system, or a combination thereof is provided from a noncarbon based energy source, from a renewable energy source, and/or from electricity.

21 Claims, 2 Drawing Sheets

Related U.S. Application Data filed on Jan. 15, 2019, provisional application No. 62/792,617, filed on Jan. 15, 2019, provisional application No. 62/792,637, filed on Jan. 15, 2019, provisional application No. 62/792,634, filed on Jan. 15, 2019, provisional application No. 62/792,612, filed on Jan. 15, 2019, provisional application No. 62/792,615, filed on Jan. 15, 2019, provisional application No. 62/792,635, filed on Jan. 15, 2019, provisional application No. 62/792,636, filed on Jan. 15, 2019, provisional application No. 62/792,619, filed on Jan. 15, 2019, provisional application No. 62/792,622, filed on Jan. 15, 2019, provisional application No. 62/792,631, filed on Jan. 15, 2019, provisional application No. 62/792,632, filed on Jan. 15, 2019.

(51) Int. Cl.

| | |
|---|---|
| *B01D 53/26* | (2006.01) |
| *B01J 4/00* | (2006.01) |
| *B01J 6/00* | (2006.01) |
| *B01J 19/24* | (2006.01) |
| *C01B 3/12* | (2006.01) |
| *C01B 3/34* | (2006.01) |
| *C01B 3/48* | (2006.01) |
| *C01B 3/56* | (2006.01) |
| *C01C 1/02* | (2006.01) |
| *C01C 1/04* | (2006.01) |
| *C07C 4/02* | (2006.01) |
| *C07C 4/04* | (2006.01) |
| *C07C 29/132* | (2006.01) |
| *C07C 29/152* | (2006.01) |
| *F25J 3/02* | (2006.01) |
| *H01M 8/04082* | (2016.01) |
| *H01M 8/0606* | (2016.01) |
| *H01M 8/0612* | (2016.01) |
| *H02J 15/00* | (2006.01) |
| *H01M 8/1007* | (2016.01) |

(52) U.S. Cl.
CPC .............. *B01J 4/008* (2013.01); *B01J 6/008* (2013.01); *B01J 19/0033* (2013.01); *B01J 19/2465* (2013.01); *C01B 3/12* (2013.01); *C01B 3/342* (2013.01); *C01B 3/48* (2013.01); *C01B 3/56* (2013.01); *C01C 1/02* (2013.01); *C01C 1/0417* (2013.01); *C01C 1/0488* (2013.01); *C07C 4/02* (2013.01); *C07C 4/04* (2013.01); *C07C 29/132* (2013.01); *C07C 29/152* (2013.01); *F25J 3/0233* (2013.01); *H01M 8/04201* (2013.01); *H01M 8/0606* (2013.01); *H01M 8/0618* (2013.01); *H02J 15/006* (2013.01); *H02J 15/008* (2020.01); *B01D 2256/16* (2013.01); *B01D 2256/245* (2013.01); *B01J 2219/00051* (2013.01); *B01J 2219/00132* (2013.01); *B01J 2219/00761* (2013.01); *B01J 2219/0871* (2013.01); *C01B 2203/0216* (2013.01); *C01B 2203/0233* (2013.01); *C01B 2203/0238* (2013.01); *C01B 2203/0244* (2013.01); *C01B 2203/0261* (2013.01); *C01B 2203/0283* (2013.01); *C01B 2203/0294* (2013.01); *C01B 2203/04* (2013.01); *C01B 2203/061* (2013.01); *C01B 2203/066* (2013.01); *C01B 2203/068* (2013.01); *C01B 2203/085* (2013.01); *C01B 2203/148* (2013.01); *H01M 8/1007* (2016.02)

(58) Field of Classification Search
CPC ...... B01J 2219/00135; B01J 2219/0803; B01J 2219/0871; B01J 2208/00389; B01J 2208/00415; Y02E 10/00; Y02E 10/10; Y02E 10/30; Y02E 10/40; Y02E 10/07; Y02E 50/00; Y02E 50/10; Y02E 50/30; Y02E 30/00
See application file for complete search history.

(56) References Cited

U.S. PATENT DOCUMENTS

| | | | | |
|---|---|---|---|---|
| 4,140,602 | A | * | 2/1979 | Lewis ................... C07C 29/149 376/148 |
| 4,158,637 | A | * | 6/1979 | Jones ....................... C10G 1/06 423/580.1 |
| 4,233,127 | A | | 11/1980 | Monahan |
| 4,434,133 | A | * | 2/1984 | Down ................... C07C 1/2076 568/301 |
| 4,684,759 | A | | 8/1987 | Lam |
| 5,059,404 | A | * | 10/1991 | Mansour ................ C10K 1/004 48/77 |
| 5,122,299 | A | | 6/1992 | Leblanc |
| 5,180,570 | A | | 1/1993 | Lee et al. |
| 5,321,191 | A | | 6/1994 | Alagy et al. |
| 5,620,670 | A | * | 4/1997 | Benham .................. C10L 1/026 518/703 |
| 6,100,303 | A | | 8/2000 | Hirotani et al. |
| 6,183,703 | B1 | | 2/2001 | Hsu et al. |
| 6,506,510 | B1 | | 1/2003 | Sioui et al. |
| 7,288,690 | B2 | | 10/2007 | Bellet et al. |
| 2004/0060301 | A1 | | 4/2004 | Aceves et al. |
| 2005/0271924 | A1 | | 12/2005 | Coors et al. |
| 2006/0116543 | A1 | | 6/2006 | Bellet |
| 2006/0207178 | A1 | | 9/2006 | Hsu |
| 2007/0204512 | A1 | * | 9/2007 | Self ......................... C01B 3/384 48/197 FM |
| 2011/0229780 | A1 | | 9/2011 | Kershaw |
| 2012/0055331 | A1 | | 3/2012 | Steele |
| 2012/0149788 | A1 | | 6/2012 | Ahmed et al. |
| 2012/0186252 | A1 | * | 7/2012 | Schmidt .................... F22B 1/18 60/676 |
| 2013/0177975 | A1 | | 7/2013 | Goetz et al. |
| 2013/0252034 | A1 | | 9/2013 | Hu et al. |
| 2015/0129805 | A1 | | 5/2015 | Karpenko et al. |
| 2015/0232999 | A1 | * | 8/2015 | Busskamp ............. C10K 1/005 205/637 |
| 2015/0275108 | A1 | | 10/2015 | Gueh |
| 2016/0017800 | A1 | * | 1/2016 | Simpson ................... C25B 1/04 422/162 |
| 2016/0122194 | A1 | * | 5/2016 | Markowz ................ H02J 3/008 422/186.21 |
| 2016/0347908 | A1 | | 12/2016 | Muller et al. |
| 2016/0369191 | A1 | | 12/2016 | Ward |
| 2017/0137355 | A1 | | 5/2017 | Sarsani et al. |

(56) References Cited

U.S. PATENT DOCUMENTS

| | | | |
|---|---|---|---|
| 2017/0362147 | A1 | 12/2017 | Won et al. |
| 2018/0237555 | A1 | 8/2018 | Buach et al. |

FOREIGN PATENT DOCUMENTS

| | | |
|---|---|---|
| CN | 102753656 | 10/2012 |
| CN | 103003192 | 3/2013 |
| CN | 103025649 | 4/2013 |
| CN | 105209373 | 12/2015 |
| CN | 107223114 | 9/2017 |
| CN | 108368037 | 8/2018 |
| EA | 029413 | 3/2018 |
| EP | 0539244 A1 | 4/1993 |
| EP | 2281793 | 2/2011 |
| EP | 3249027 | 11/2017 |
| EP | 3017025 | 3/2018 |
| JP | BS4614246 | 4/1971 |
| JP | AS54136574 | 10/1979 |
| JP | AS62089634 | 4/1987 |
| JP | H0565237 | 3/1993 |
| JP | AH5222379 | 8/1993 |
| JP | H05222379 | 8/1993 |
| JP | AH9235564 | 9/1997 |
| JP | A2003504485 | 2/2003 |
| JP | 2003504485 | 4/2003 |
| JP | A2004524338 | 8/2004 |
| JP | A2005515295 | 5/2005 |
| JP | A2009531529 | 9/2009 |
| JP | 4585729 B2 | 11/2010 |
| JP | 2013537042 A | 9/2013 |
| KR | 2014-0140562 | 3/2012 |
| RU | 2203214 | 4/2003 |
| RU | 2005/102272 | 7/2006 |
| RU | 2501841 | 12/2013 |
| RU | 2534092 | 11/2014 |
| RU | 2570659 | 12/2015 |
| RU | 2617772 | 4/2017 |
| SU | 823377 | 4/1981 |
| WO | WO 02/074721 | 9/2002 |
| WO | WO 03/062352 | 7/2003 |
| WO | WO 2007117919 | 10/2007 |
| WO | WO 2008/122399 | 10/2008 |
| WO | WO 2011/083333 | 7/2011 |
| WO | WO 2013/124092 | 8/2013 |
| WO | WO 2016/209508 | 12/2016 |
| WO | WO 2018/234971 | 12/2018 |

OTHER PUBLICATIONS

Bazzanella et al., "Low carbon energy and feedstock for the European chemical industry", pp. 1-168, 2017.
Doyle, "BASF announces four research projects for reducing CO2 emissions—News—The Chemical Engineer", pp. 1-14, 2019.
Ekejiuba "Evaluation of the Exact Production Quantity of Nitrogen Fertilizer in Real-Time from any Particular Associated Gas Flare Volume in Nigeria" International Journal of Applied Science and Technology vol. 7, No. 3, Sep. 3, 2017, pp. 87-100.
Extended European Search Report issued in corresponding European Application No. 20741429.3 dated Jan. 9, 2023.
Hobson, et al. "Renewable methanol report" *Methanol Institute*, Dec. 2018, pp. 1-26.
Hydrogen Council "How hydrogen empowers the energy transition" Jan. 2017 https://hydrogencouncil.com/wp-content/uploads/2-17/06/Hydrogen-Council-Vision-Document.pdf.
International Search Report and Written Opinion issued in corresponding International application PCT/US2020/013525 mailed May 18, 2020.
Lewis, Jonathan "Fuels Without Carbon Prospects and the Pathway Forward for Zero-Carbon Hydrogen and Ammonia Fuels" Dec. 2018 https://www.catf.us.resouce/fuels-ithout-carbon/.
Mortensen, et al. "Direct Hysteresis Heating of Catalytically Active Ni—Co Nanoparticles as Steam Reforming Catalyst" Industrial & Engineering Chemistry Research vol. 56, No. 47, Nov. 15, 2017, pp. 14006-14013.
Office Action issued in corresponding Chinese Application No. 202080021299.2, dated Jun. 7, 2023.
Pattabathula, et al. "Introduction to Ammonia Production" Chemical Engineering Progress Sep. 2016, pp. 69-75.
Weinian, Feng., et al. "Encyclopedia of Chemical Engineering" (vol. 3 "tool materials _ Power Generation Doa fa", pp. 4007-4408, Chemical Industry Press, Mar. 1993. (no translation available).
Wismann, et al., "Electrified methane reforming: A compact approach to greener industrial hydrogen production" *Science*, vol. 364, No. 6442, May 24, 2019, pp. 756-759.
Zimmermann et al., "Ethylene" In: Ullmann's Encyclopedia of Wiley-VCH Industrial Chemistry, 2009.

* cited by examiner

USE OF RENEWABLE ENERGY IN THE PRODUCTION OF CHEMICALS

CROSS-REFERENCE TO RELATED APPLICATIONS

This application is a national phase application under 35 U.S.C. § 371 of International Application No. PCT/US2020/013525 filed Jan. 14, 2020, which claims the benefit of priority of U.S. Provisional Patent Application No. 62/792,612 filed Jan. 15, 2019, U.S. Provisional Patent Application No. 62/792,615 filed Jan. 15, 2019, U.S. Provisional Patent Application No. 62/792,617 filed Jan. 15, 2019, U.S. Provisional Patent Application No. 62/792,619 filed Jan. 15, 2019, U.S. Provisional Patent Application No. 62/792,622 filed Jan. 15, 2019, U.S. Provisional Patent Application No. 62/792,627 filed Jan. 15, 2019, U.S. Provisional Patent Application No. 62/792,631 filed Jan. 15, 2019, U.S. Provisional Patent Application No. 62/792,632 filed Jan. 15, 2019, U.S. Provisional Patent Application No. 62/792,633 filed Jan. 15, 2019, U.S. Provisional Patent Application No. 62/792,634 filed Jan. 15, 2019, U.S. Provisional Patent Application No. 62/792,635 filed Jan. 15, 2019, U.S. Provisional Patent Application No. 62/792,636 filed Jan. 15, 2019, U.S. Provisional Patent Application No. 62/792,637 filed Jan. 15, 2019, all of which are hereby incorporated by reference in their entirety.

TECHNICAL FIELD

The present disclosure relates to the use of non-carbon-based or renewable energy in the production of chemicals; more particularly, the present disclosure relates to the electrification of a chemical synthesis plant; still more particularly, the present disclosure relates to a reduction in environmental emissions, such as carbon dioxide, by reducing the combustion of hydrocarbons (e.g., natural gas/fossil fuels) for fuel in a chemical synthesis plant.

BACKGROUND

Chemical synthesis plants are utilized to provide a variety of chemicals. Often, a dedicated fuel is burned or 'combusted' to provide heat of reaction for chemical synthesis, energy to heat one or more process streams, energy to vaporize liquids (e.g., boil water used as a diluent), energy to do work (e.g., drive a compressor or pump), or energy for other process operations throughout the chemical synthesis plant. Such burning or combustion of fuels results in the production of flue gases, which can be harmful to the environment, and also results in a loss of energy efficiency of the process. Likewise, steam is often conventionally utilized as a plant-wide heat and/or energy transfer fluid within chemical synthesis plants. The steam utilized for the heat and/or energy transfer is often produced via the combustion of a fuel, resulting in the production of additional flue gas and further energy efficiency losses during the chemical synthesis. Additionally, the use of a material that could otherwise be utilized as a reactant for combustion as a fuel also reduces an amount of the desired chemical product produced in the chemical synthesis plant from a given amount of the material. Accordingly, a need exists for enhanced systems and methods of chemical synthesis whereby an amount of fuels, especially fossil fuels, burned to provide energy is reduced or eliminated. Desirably, such systems and methods also provide for an increase in energy efficiency and/or a decrease in emissions, such as emissions of greenhouse gases (GHG), by the chemical synthesis plant.

SUMMARY

Herein disclosed is a chemical synthesis plant comprising: one or more reactors configured for producing, from one or more reactants, a process stream comprising at least one chemical product; a feed preparation system configured to prepare one or more feed streams comprising one or more of the one or more reactants for introduction into the one or more reactors; and/or a product purification system configured to separate the at least one chemical product from reaction byproducts, unreacted reactants, or a combination thereof within the process stream, wherein the chemical synthesis plant is configured such that a majority (e.g., greater than 50, 60, 70, 80, 90, or 100%) of the net energy needed for heating, cooling, compressing, or a combination thereof utilized via the one or more reactors, the feed preparation system, the product purification system, or a combination thereof is provided from a non-carbon based energy source, from a renewable energy source, and/or from electricity.

Also disclosed herein is a chemical synthesis plant wherein a majority (e.g., greater than 50, 60, 70, 80, 90, or 100%) of the net energy input conventionally provided by the combustion of a fuel is provided by electricity.

Further disclosed herein is a chemical synthesis plant wherein a majority of the net energy conventionally provided by the combustion of a fuel is provided by a non-carbon based energy source, a renewable energy source, and/or renewable electricity.

Also disclosed herein is a chemical synthesis plant comprising: one or more reactors configured for producing, from one or more reactants, a process stream comprising at least one chemical product; a feed preparation system configured to prepare one or more feed streams comprising one or more of the one or more reactants for introduction into the reactor; and/or a product purification system configured to separate the at least one chemical product from reaction byproducts, unreacted reactants, or a combination thereof within the process stream, wherein the chemical synthesis plant is configured: (a) such that no combustion flue gas is produced; (b) without a substantially plant-wide steam system; (c) such that no steam is utilized therein to perform mechanical work; (d) such that any steam utilized as a diluent and/or reactant within the chemical synthesis plant is generated with electricity; (e) such that any steam utilized as a diluent and/or a reactant is superheated electrically to provide heat/raise the temperature of a process stream; (f) such that heat obtained from cooling process streams is utilized solely to preheat other process streams; or (g) any combination of (a)-(f).

BRIEF DESCRIPTION OF THE DRAWINGS

For a more complete understanding of the present disclosure and the advantages thereof, reference is now made to the following brief description, taken in connection with the accompanying drawings and detailed description, wherein like reference numerals represent like parts.

DETAILED DESCRIPTION

Figure 1:
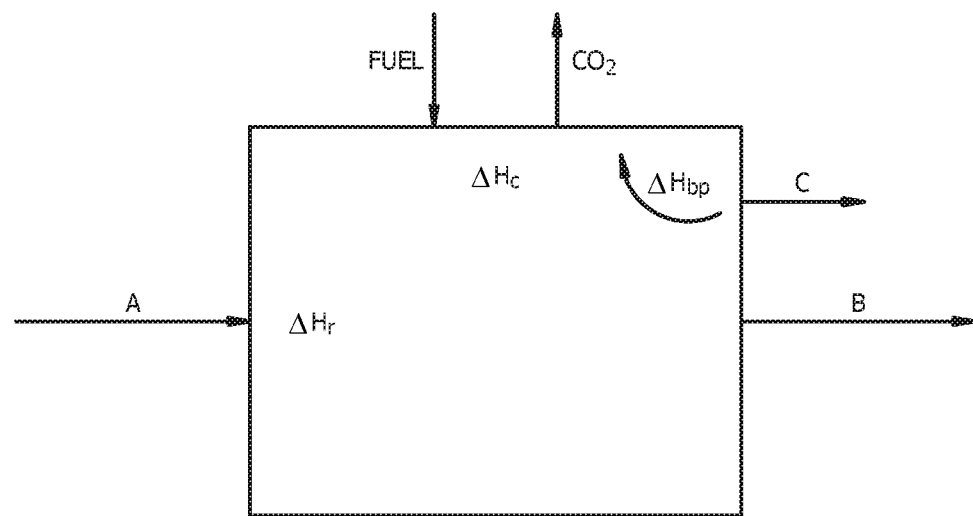
FIG. 1 shows a conceptual diagram of a typical prior art chemical process.

It should be understood at the outset that although an illustrative implementation of one or more embodiments are provided below, the disclosed compositions, methods, and/or products may be implemented using any number of techniques, whether currently known or not yet in existence. The disclosure should in no way be limited to the illustrative implementations, drawings, and techniques illustrated hereinbelow, including the exemplary designs and implementations illustrated and described herein, but may be modified within the scope of the appended claims along with their full scope of equivalents.

While the following terms are believed to be well understood by one of ordinary skill in the art, the following definitions are set forth to facilitate explanation of the presently disclosed subject matter. Unless defined otherwise, all technical and scientific terms used herein have the same meaning as commonly understood to one of ordinary skill in the art to which the presently disclosed subject matter belongs.

As utilized herein, an 'intermittent energy source' or 'IES' is any source of energy that is not continuously available for conversion into electricity and outside direct control because the used energy cannot be stored or is economically undesirable. The availability of the intermittent energy source may be predictable or non-predictable. A renewable intermittent energy source is an intermittent energy source that is also a source of renewable energy, as defined hereinbelow. 'Intermittent electricity' refers to electricity produced from an IES.

As utilized herein, 'renewable energy' and 'non-fossil based energy ($E_{NF}$)' includes energy derived from a sustainable energy source that is replaced rapidly by a natural, ongoing process, and nuclear energy. Accordingly, the terms 'renewable energy' and 'non-fossil based energy ($E_{NF}$)' refer to energy derived from a non-fossil fuel based energy source (e.g., energy not produced via the combustion of a fossil fuel such as coal or natural gas), while 'non-renewable' or 'fossil based energy ($E_F$)' is energy derived from a fossil fuel-based energy source (e.g., energy produced via the combustion of a fossil fuel). Fossil fuels are natural fuels, such as coal or gas, formed in the geological past from the remains of living organisms. Accordingly, as utilized herein, 'renewable' and 'non-fossil based energy ($E_{NF}$)' include, without limitation, wind, solar power, water flow/movement, or biomass, that is not depleted when used, as opposed to 'non-renewable' energy from a source, such as fossil fuels, that is depleted when used. Renewable energy thus excludes fossil fuel based energy ($E_F$) and includes biofuels.

As utilized herein, 'non-carbon based energy ($E_{NC}$)' is energy from a non-carbon based energy source (e.g., energy not produced via the combustion of a carbon-based fuel such as a hydrocarbon), while carbon based energy ($E_C$) is energy from a carbon-based energy source (e.g., energy produced via the combustion of a carbon-based fuel such as a hydrocarbon). Nuclear energy is considered herein a renewable, non-fossil ($E_{NF}$) based energy and a non-carbon based energy ($E_{NC}$). Carbon-based energy ($E_C$) can thus be renewable (e.g., non-fossil fuel based) or non-renewable (e.g., fossil fuel-based). For example, various carbon-based biofuels are herein considered renewable, carbon-based energy sources.

As utilized herein, 'renewable electricity' indicates electricity produced from a renewable energy source, while 'non-renewable electricity' is electricity produced from a non-renewable energy source. As utilized herein 'non-carbon based electricity' indicates electricity produced from a non-carbon based energy source, while 'carbon-based electricity' is electricity produced from a carbon-based energy source.

For example, in embodiments, renewable electricity and/or heat throughout the herein-disclosed chemical synthesis plant can be provided by the combustion of renewable hydrocarbons that come from renewable (e.g., biological) sources. For example, renewable electricity can, in embodiments, be produced via the combustion of an $E_{NF}/E_C$ energy source comprising methane produced in a digester fed with agricultural wastes. Likewise, in embodiments, an $E_{NF}/E_C$ energy source comprising synthesis gas produced using short cycle carbon waste materials can be utilized as a fuel (e.g., combusted to produce renewable electricity and/or heat). Desirably, the carbon dioxide generated by such combustion is recaptured (e.g., by the growth of a new crop).

As utilized herein, 'externally' combusting a fuel refers to combusting a fuel outside of a reactor, e.g., in a furnace. Combustion as a part of the primary reaction (e.g., combustion which takes place with reforming in autothermal reforming (ATR)) would not be considered 'externally' combusting. As utilized herein, a 'dedicated' fuel is a fuel or portion of a feed stream introduced solely to provide fuel value (e.g., combustion heat) and not be converted into product.

As utilized herein, 'heat transfer steam ($S_{HT}$)' indicates steam produced solely or primarily as an energy or heat transfer medium (e.g., steam not utilized as a diluent and/or reactant).

As utilized herein, 'net' heat input or removal refers to heat input or removal that results in primary energy consumption, e.g., heat input or removal not provided from another section or stream of the plant, e.g., not provided via heat exchange with another process stream. Similarly, 'net' energy refers to energy that results in primary energy consumption, e.g., energy not provided from another section or stream of the plant, e.g., thermal energy not provided via heat exchange with another process stream.

As utilized herein, 'powering' indicates supplying with mechanical and/or electrical energy.

As utilized herein, 'heating' indicates supplying with thermal energy. As utilized herein 'cooling' indicates the removal of thermal energy therefrom. As utilized herein, 'direct' heating or cooling refer to heating or cooling without the use of a heat transfer medium/fluid; 'indirect' heating or cooling refer to heating or cooling via a heat transfer medium/fluid.

As utilized herein, 'most' or 'a majority' indicates more than 50% or more than half.

As utilized herein, a 'desired' parameter (e.g., desired temperature) may refer to an intended or target value for the parameter, for example a predetermined value such as a set-point value used for process control.

Amount of electricity consumed: References to consumption of electricity may refer to a rate at which electricity is used (e.g., in MW), as measured at a particular location. For example, a rate may be calculated at the boundary of each electrified furnace or at an overall olefin synthesis plant boundary. This calculation may consider all electricity used within that location.

Flue gas: A mixture of gases that may be produced by the burning of fuel or other materials in a power station and/or industrial plant, where the mixture of gases may be extracted via ducts.

Flue gas heat recovery: Flue gas heat recovery may refer to the extraction of useful thermal energy from hot flue gases, for example by passing said hot flue gas over one or more heat exchangers to raise the temperature of a cooler process fluid and/or change the phase of said fluid (e.g., boil water to raise steam). Any energy remaining in the flue gas after any flue gas heat recovery may be termed flue gas (energy) loss. A flue gas heat recovery section may be the equipment and corresponding location of said equipment used to recover flue gas heat. A lack of flue gas heat recovery section may mean there is no equipment or area where heat is recovered from hot flue gases.

Convection section: A convection section may be a portion of a furnace (e.g., steam cracking furnace or reforming furnace) where heat is recovered from hot flue gases by convective heat transfer. A lack of convection section may mean that there is no equipment or area where heat is recovered by convective heat transfer from hot flue gases.

"Steam-free" or "Substantially Steam-free": "Steam free" may refer to a process where steam is not used to transfer energy from one process operation to another, or to bring energy into the process from outside. "Substantially steam-free" may mean that the use of steam to transfer energy from one process operation to another or to bring energy into the process from outside has been minimized such that the sum of all energy transfers using steam amount to less than approximately 10%, approximately 20%, or approximately 30% of the net energy provided. Steam used as a reactant, a diluent, obtained as a product, or directly mixed with a process stream may be termed "process steam" and is not included in this definition.

Primary energy transfer medium: A primary energy transfer medium may be a substance that is used to move energy in the form of thermal energy from one process operation to another, or to bring energy into a process. Note that a substance may serve more than one purpose in a process such as acting as a reactant or reaction diluent whilst also acting as a medium to transfer heat from one process operation to another. In such instances, the use of steam as reactant or diluent may be considered primary and the effect of also transferring heat may be considered secondary.

Resistive heating: Resistive heating may be heating by means of passing electric current through resistive units.

Inductive heating: Induction heating may be a process of heating an electrically conducting object (usually a metal) by electromagnetic induction.

Radiant heating: Radiant heating may be a process of heating an object via radiation from one or more hotter objects.

Externally combusting: Externally combusting may mean burning fuel to generate heat and transferring this heat to a process fluid across a surface (e.g., a tube wall) such that combustion products do not mix with the process fluid.

Thermoelectric device: A thermoelectric device may be a device for the direct conversion of temperature differences to electric voltage (or vice versa) across a thermocouple.

Isothermal operation: Isothermal operations may be operations at a constant temperature. Isothermal operation can keep temperature within 0.5%, 1%, 2%, 3%, 4%, 5% up to 10% of the predetermined operation temperature.

Convective heat transfer: Convective heat transfer may be the movement of heat from one place to another by the movement of a fluid or fluids.

Although the majority of the above definitions are substantially as understood by those of skill in the art, one or more of the above definitions can be defined hereinabove in a manner differing from the meaning as ordinarily understood by those of skill in the art, due to the particular description herein of the presently disclosed subject matter.

FIG. 1 shows a conceptual diagram of a typical traditional chemical process. The goal of this process is to convert feed A into product B, although often some byproducts (indicated as stream C) are also produced.

The unit operations used to effect this transformation require significant amounts of energy. Conventionally, this energy is primarily supplied by burning a fuel, often natural gas, to generate heat, denoted in FIG. 1 as $\Delta H_c$ (e.g., heat of combustion). This results in the undesirable production and emission of carbon dioxide ($CO_2$). Additional energy may be supplied by the heat of reaction, $\Delta H_r$, if the reaction is exothermic; if the reaction is endothermic, an additional amount of energy equal to $\Delta H_r$ will need to be added. The total energy balance may also be affected if some byproducts are burned to produce energy, indicated as $\Delta H_{bp}$. However, many chemical processes, even those involving exothermic reactions, are net energy consumers and thus require an external source of energy (typically provided by a hydrocarbon fuel(s)) to provide net process energy.

Electricity is usually only a small external input into most chemical production processes. Internal electrical requirements, such as for lighting or control, are usually so small as to be negligible, and in those few processes which require large amounts of electricity, for example, electrochemical reactors (e.g., the chlor-alkali process to make chlorine ($Cl_2$) and sodium hydroxide (NaOH)), this electricity is commonly generated within the plant boundaries by the combustion of hydrocarbons, and, even when not generated within the plant boundaries, if the electricity is obtained by the combustion of hydrocarbons rather than renewably, such use of electricity is equivalent in terms of energy efficiency and $CO_2$ emissions to on-site production of the electricity via hydrocarbon combustion.

Within most chemical production processes, energy consumption can conveniently be divided into three main categories. In the first such broad category, referred to herein as first category C1, heat is supplied directly as thermal energy by the combustion of a fuel (e.g., natural gas/fossil fuels) in a furnace. (As utilized, here, 'directly' indicates the absence of an intermediate heat transfer medium, such as steam.) These furnaces are often operated at high temperature and require large heat fluxes. The energy efficiency of such furnaces is limited by the heat losses in the furnace flue gas. Even where these heat losses are minimized by the cooling of the flue gas to recover energy, for example to generate steam or provide process heating, the conversion of the chemical energy contained in the fuel to usable thermal energy generally does not exceed 85 to 90%, even with substantial investment and loss of design and operating flexibility.

The second broad category, referred to herein as second category C2, of energy consumption in chemical processes comprises the heating of various chemical streams, primarily either to raise the temperature thereof to a desired reaction temperature or to provide energy for separations, most commonly distillation. Although some of this heat can be obtained by exchange with other chemical streams, it is most typically provided either by steam generated directly by the combustion of hydrocarbon fuels (e.g., natural gas/ fossil fuels) or by heat transfer from the flue gas from high-temperature furnaces (e.g., from category C1). Most modern chemical processes include a relatively complicated steam system (or other heat transfer fluid system which will generically be referred to herein for simplicity as a steam heat transfer system) to move energy from where it is in excess to where it is needed. This steam system may include multiple pressure levels of steam to provide heat at different temperatures, as well as a steam and condensate recovery system, and is subject to corrosion, fouling, and other operational difficulties, including water treatment and contaminated condensate disposal. The fraction of the energy contained in the steam that can be used to heat process streams is generally limited to 90 to 95% by practical constraints on heat transfer, steam condensation, and boiler water recycle. If the steam was generated by an on-purpose external boiler, at most 80 to 85% of the chemical energy contained in the fuel will be used as heat by the chemical process, since an additional 10 to 15% or more will be lost to flue gas as in first category C1.

The third major category, referred to herein as third category C3, of energy usage in chemical processes is energy utilized to perform mechanical work. This work is primarily utilized for pressurizing and moving fluids from one place to another, and is used to drive rotating equipment such as pumps, compressors, and fans. This third category C3 also includes refrigeration equipment, since it is primarily powered by compression. In most chemical facilities, the energy for this work is provided by steam, obtained either by heat transfer with hot process streams, by heat transfer with partially-cooled flue gas streams from a furnace (e.g., in the convection section) in category C1, or directly from the combustion of hydrocarbons (e.g., natural gas/fossil fuels) in an on-purpose external boiler. Because of limitations on the conversion of thermal energy to mechanical work, the energy efficiency of these uses relative to the contained chemical energy of the hydrocarbons used as fuel is low, typically only 25 to 40%.

It has been unexpectedly discovered that using electricity (e.g., renewable and/or non-renewable electricity) to replace energy obtained from a hydrocarbon fuel in a chemical process can improve the process by increasing overall energy efficiency, while decreasing carbon dioxide emissions. In some cases, using electricity (e.g., renewable and/or non-renewable electricity) to replace energy obtained from a hydrocarbon fuel in a chemical process can also improve reliability and operability, decrease emissions of, for example, NOx, SOx, CO, and/or volatile organic compounds, and/or decrease production costs (e.g., if low-cost electricity is available).

According to embodiments of this disclosure, heat conventionally supplied as thermal energy by the combustion of a fuel (e.g., natural gas/fossil fuels) in a furnace and/or other heating in first category C1 is replaced by electrical heating. Electrical heat, electrical heating, generating heat electrically, electrical heater apparatus, and the like refer to the conversion of electricity into thermal energy available to be applied to a fluid. Such electrical heating includes, without limitation, heating by impedance (e.g., where electricity flows through a conduit carrying the fluid to be heated), heating via ohmic heating, plasma, electric arc, radio frequency (RF), infrared (IR), UV, and/or microwaves, heating by passage over a resistively heated element, heating by radiation from an electrically-heated element, heating by induction (e.g., an oscillating magnetic field), heating by mechanical means (e.g. compression) driven by electricity, heating via heat pump, heating by passing a relatively hot inert gas or another medium over tubes containing a fluid to be heated, wherein the hot inert gas or the another medium is heated electrically, or heating by some combination of these or the like.

According to embodiments of this disclosure, the utilization of steam (or another heat transfer fluid) as in second category C2 is eliminated and/or any steam (or other fluid) utilized solely as an intermediate heat transfer medium is electrically produced or heated (e.g., via electrical heating of water).

According to embodiments of this disclosure, conventional rotating equipment (e.g., steam turbines) utilized in third category C3 is replaced with electrically driven apparatus. According to embodiments of this disclosure, heat removal in third category C3 is replaced by electrically-powered heat removal, e.g., cooling and/or refrigeration. Electrical cooling, electrical coolers, removing heat electrically, electrical cooling or refrigeration apparatus, and the like refer to the removal of thermal energy from a fluid. Such electrical cooling includes, without limitation, cooling by electrically powered apparatus. For example, and without limitation, electrical cooling can be provided by powering a refrigeration cycle with electricity, wherein a refrigerant is compressed by an electrically powered compressor. As another example, electrical cooling can be provided by powering a cooling fan that blows air, wherein the air cools a process fluid or element. In embodiments, electrical heating and cooling can be effected by any electrical source.

Figure 2:
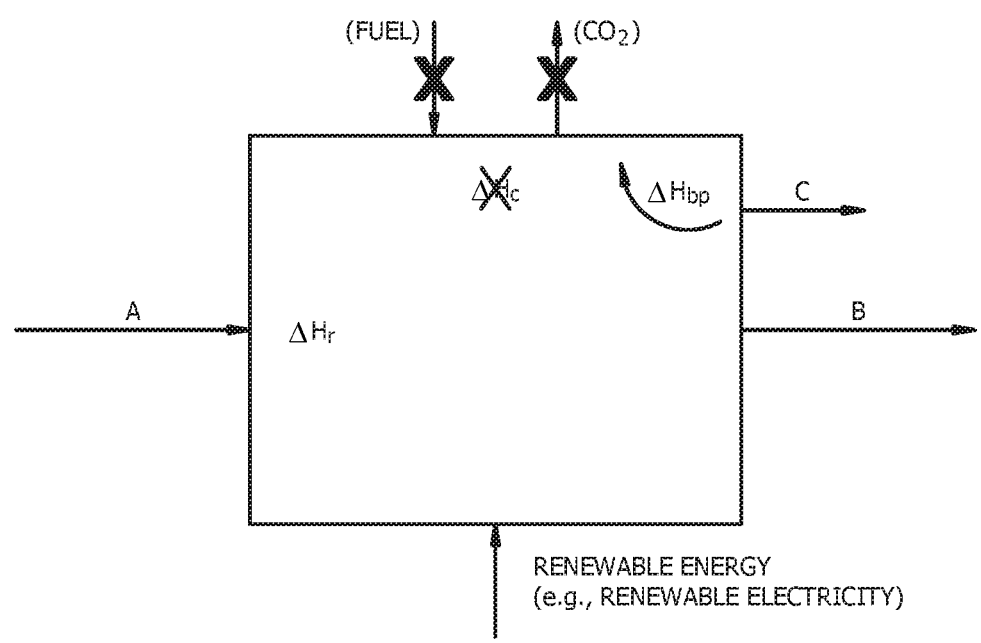
FIG. 2 shows a conceptual diagram of a chemical process powered by renewable energy, according to embodiments of this disclosure.

FIG. 2 is a schematic of a chemical process powered by renewable energy, according to embodiments of this disclosure. As shown in FIG. 2, a process driven by renewable energy can, in embodiments, appear similar to a conventional chemical process. However, a portion, a majority, or, in some cases, substantially all of the energy input supplied by fuel can be replaced by renewable energy and/or by renewable electricity. Such replacement of fuel input by non-carbon based energy, renewable energy, and/or renewable electricity will allow for a significant decrease in $CO_2$ emissions, in embodiments. In embodiments, any available form of renewable energy can be employed. However, the gains may be greatest if renewable electricity is utilized. The renewable energy can be obtained from, for example and without limitation, solar power, wind power, or hydroelectric power. Other types of renewable energy can also be applied in chemical plants according to embodiments of this disclosure. For example, in embodiments, concentrated solar power, geothermal energy, and/or the use of direct solar heating can be used to provide thermal energy and to decrease $CO_2$ emissions.

One of the main advantages to supplying needed energy via (e.g., renewable) electricity can be that the energy efficiency of the process will increase. Table 1 shows the energy efficiency of unit operations exemplifying the three categories of energy use in a chemical plant described above as C1, C2, and C3. It can be seen from Table 1 that the efficiency of each of the three categories of energy consumption is greater when electrical power is used. The gain can be greatest when steam drives for rotating equipment are replaced, according to embodiments of this disclosure, with electrical motors (as in third category C3, discussed hereinabove), which can operate with as much as three times the energy efficiency of steam drives. These gains are only realized when the electricity is derived from non-carbon based renewable sources, since the generation of electricity from carbon-based fuel combustion is only 30 to 45% energy efficient. Energy efficiency gains when using renewable electricity for heating applications (as in first category C1 and second category C2, discussed hereinabove) are smaller, but still significant. The net result is that less total energy will be used if renewable energy is used in place of carbon-based fuels (e.g., natural gas or other hydrocarbons).

TABLE 1

Energy Efficiency of Unit Operations

| Use | Efficiency from Hydrocarbon Combustion | Efficiency from Electricity According to This Disclosure |
|---|---|---|
| C1: Direct Heating | up to 80-90% | 95+% |
| C2: Heating with Steam | up to 80-95% | 95+% |
| C3: Rotating Equipment | 25-40% | 90-95% |

According to this disclosure, non-carbon based energy, renewable energy, and/or electricity (e.g., from renewable and/or non-renewable sources) can be utilized rather than conventional energy sources in categories C1, C2, and/or C3 described hereinabove. In embodiments, electrification is utilized for a majority of or substantially all utilities. In embodiments, electrification is utilized for a majority of or substantially all unit operations. In embodiments, electrification is utilized for a majority of or substantially all utilities and unit operations. In embodiments, electrification is utilized for a majority of or substantially all process applications, engines, cooling and/or heating (e.g., electrically driven heat pumps, refrigeration, electrical heating), radiation, storage systems, or a combination thereof.

In embodiments, the non-carbon based and/or renewable energy source comprises wind, solar, geothermal, hydroelectric, nuclear, tide, wave, ocean thermal gradient power, pressure-retarded osmosis, or a combination thereof. In embodiments, the non-carbon based energy source comprises hydrogen. In embodiments, electricity for electrification as described herein is produced from such a renewable and/or non-carbon based energy source. In embodiments, some or all of the electricity is from a non-renewable and/or carbon-based source, such as, without limitation, combustion of hydrocarbons (e.g., renewable or non-renewable hydrocarbons), coal, or hydrogen derived from hydrocarbons (e.g., renewable or non-renewable hydrocarbons).

The majority of the $CO_2$ emitted from most chemical plants is a result of fossil fuel combustion to provide energy for the plant. An additional benefit of using renewable energy in chemical synthesis as per embodiments of this disclosure is that the amount of greenhouse gases emitted will be significantly (e.g., by greater than or equal to at least 5, 10, 20, 30, 40, 50, 60, 70, 80, 90, or 100%) reduced relative to an equivalent conventional chemical synthesis plant or method in which hydrocarbons and/or fossil fuel(s) may be combusted. The burning of hydrocarbons (e.g., natural gas, methane) to generate energy results in the production of carbon dioxide ($CO_2$); this production can be reduced or avoided by the use of renewable energy according to embodiments of this disclosure. In embodiments of this disclosure, the amount of $CO_2$ produced per ton of product produced is reduced less than or equal to about to 1.6, 1.5, 1.4, 1.3, 1.2, 1.1, 1.0, 0.75, 0.5, 0.30, 0.25, 0.2, 0.1, 0.05, or 0 tons $CO_2$ per ton chemical product. Furthermore, in embodiments of this disclosure, the use of renewable energy frees up these hydrocarbons (e.g., natural gas, methane) typically burned for fuel for use as a chemical feedstock (e.g., to make methanol), which is a higher value use.

The use of renewable electricity in the production of chemicals can also lead to operational advantages. For example, in embodiments, electric power can be utilized to provide a more accurate and tunable input of heat, for example to control the temperature profile along a reactor or to change the temperature of specific trays in a distillation column. In embodiments, the use of electric heating in a reaction section (e.g., in a pyrolysis reaction section) leads to better controlled decoking and/or faster decoking. Without limitation, other examples include the use of electric powered refrigeration units to increase the efficiency of separations, and the replacement of inefficient stand-by gas-fired boilers with quick-acting on-demand electrical heaters and steam generators and for other utility uses. The use of electricity may also allow for significant operational advantages during start-up or shut-down, or to respond to process variability. In general, electricity as an energy source can be applied in specific locations and in precise and tunable amounts with a rapid response to process changes, leading to a variety of advantages over the use of thermal/combustion energy.

The use of renewable electricity according to embodiments of this disclosure can also increase the energy efficiency of utilities that supply energy to more than one chemical plant (e.g., an olefin synthesis plant and a nearby ammonia synthesis plant or an olefin synthesis plant and a nearby methanol synthesis plant). For example, if the compressors in an air separation unit that provides oxygen and nitrogen to several different production facilities are powered with renewable electricity, significant energy gains can be achieved relative to supplying this power with steam derived from the combustion of natural gas.

Energy recovery may be provided, in embodiments, via high temperature heat pumps or vapor recompression. The plant may further comprise heat and/or energy storage, for example, for use when an intermittent energy source (IES) is utilized. In embodiments, waste heat can be upgraded to usable temperature levels via electrically driven heat pumps. In other embodiments, energy can be recovered as electricity when process stream pressures are reduced by using a power-generating turbine instead of a control valve. In other embodiments, energy can be recovered as electricity using thermoelectric devices.

The use of renewable electricity to replace natural gas or other hydrocarbons as a source of energy, according to embodiments of this disclosure, can be done as part of a retrofit of an existing chemical process (e.g., an existing methanol, olefins, or ammonia synthesis plant) or as an integral component of the design of a new chemical plant (e.g., a new methanol, olefins, or ammonia synthesis plant). In a retrofit, opportunities for using renewable energy can depend on elements of the existing design, such as the steam system; in a retrofit, careful examination of the entire energy balance and steam system will be required, as electrifying individual pieces of equipment without regard to these considerations may result in energy inefficiencies. In embodiments, as seen in Table 1, the highest efficiency gains are achieved by replacing steam drives for rotating equipment (e.g., in third category C3) with electric motors. However, differing objectives may lead to different choices in partial electrification; in embodiments, in some instances greater $CO_2$ reductions at the expense of smaller increases in energy efficiency may sometimes be realized by first replacing hydrocarbon-fired furnaces (e.g., in first category C 1). In embodiments, if thermal energy and/or steam are obtained from more than one hydrocarbon source, the most advantageous operation can be achieved by eliminating the most expensive and/or polluting fuel sources first. How much renewable energy can be included and to what extent existing fuel consumption and carbon dioxide ($CO_2$) emissions can be decreased can vary depending on the application, and will be within the skill of those of skill in the art upon reading this disclosure.

In embodiments, planning for the use of renewable energy in the design of a grass-roots chemical facility (e.g., a grass-roots methanol, olefins, or ammonia synthesis plant) can allow for more significant opportunities for better energy efficiency and lower $CO_2$ emissions. In embodiments, powering all rotating equipment (e.g., in third category C3) with electricity is utilized to realize large gains in energy efficiency. In embodiments, substantially all (or a majority, or greater than 40, 50, 60, 70, 80, or 90%) electric heating (e.g., in first category C1 and/or second category C2) is utilized, and the inefficiencies due to the loss of heat in flue gas are substantially reduced or even avoided. In embodiments, the use of steam generated via the combustion of a fossil fuel (e.g., in second category C2) can be minimized or avoided altogether. In embodiments, a change in catalyst and/or a modification of reactor operating conditions is utilized to allow for less heat generation in a reactor and/or the production of fewer byproducts that are burned. In embodiments, a plant (e.g., a methanol, olefins, or ammonia synthesis plant) design based on the use of renewable electricity allows for enhanced optimization of separations operations, since the relative costs of compression and refrigeration are changed via utilization of renewable electricity as per this disclosure. Such enhanced separations can, in embodiments, also allow for further capture of minor byproducts from vent streams, freeing these minor products up for further use as feedstocks or products. Furthermore, the use of low-cost electricity, according to embodiments of this disclosure, may allow for the introduction of novel technologies such as, without limitation, hybrid gas and electric heaters, variable speed compressor drives, distributed refrigeration, heat pumps, improved distillation columns, passive solar heating of fluids, precise control of reactor temperature profiles, new materials of construction, and quench or cooling using electrically refrigerated diluents. If the cost of electricity is sufficiently low, utilization of such electricity as taught herein may favor the introduction of new electrochemical processes. For new construction, it may be less capital intensive to drive processes electrically, due, for example, to the lack of a (e.g., plant-wide) steam distribution system.

According to embodiments of this disclosure, non-carbon based energy, renewable energy, and/or electricity (renewable, non-renewable, carbon-based, and/or non-carbon based electricity) can be used in the production of nearly every chemical, including but not limited to methanol, ammonia, olefins (e.g., ethylene, propylene), aromatics, and polymers. Non-carbon based energy, renewable energy, and/or electricity can also be used, in embodiments, in the preparation of feedstocks for chemicals and for fuels production, such as in methyl tert-butyl ether (MTBE) synthesis, cracking, isomerization, and reforming. In such embodiments, some (e.g., at least about 10, 20, 30, 40, or 50%), a majority (e.g., at least about 50, 60, 70, 80, 90, or 95%), or all (e.g., about 100%) of the heating throughout the plant/process or a section thereof can be provided by electrical heating and/or some (e.g., at least about 10, 20, 30, 40, or 50%), a majority (e.g., at least about 50, 60, 70, 80, 90, or 95%), or all (e.g., about 100%) of the cooling throughout the plant/process or a section thereof can be provided by electrical cooling as described hereinabove. Disclosed hereinbelow is the use of renewable energy, non-carbon based energy, and/or electricity in chemical synthesis applications.

A generalized chemical synthesis plant according to embodiments of this disclosure will now be described with reference to FIG. 3, which is a schematic of a chemical synthesis plant I, according to embodiments of this disclosure. Without limitation, in specific embodiments, the at least one chemical product comprises ethylene produced, for example, by cracking in one or more cracking reactors (e.g., via an olefin synthesis) as described in U.S. Provisional Patent Application Nos. 62/792,612 and 62/792,615, entitled *Use of Renewable Energy in Olefin Synthesis*, which are being filed on January 15, 2019, the disclosure of each of which is hereby incorporated herein for purposes not contrary to this disclosure); ammonia produced, for example, in one or more ammonia synthesis reactors (e.g., via an ammonia synthesis as described in U.S. Provisional Patent Application Nos. 62/792,617 and 62/792,619, entitled *Use of Renewable Energy in Ammonia Synthesis*, which are being filed concurrently herewith, the disclosure of each of which is hereby incorporated herein for purposes not contrary to this disclosure); methanol produced, for example, in one or more methanol synthesis reactors (e.g., via a methanol synthesis as described in U.S. Provisional Patent Application Nos. 62/792,622 and 62/792,627, entitled *Use of Renewable Energy in Methanol Synthesis*, which are being filed on Jan. 15, 2019, the disclosure of each of which is hereby incorporated herein for purposes not contrary to this disclosure); propylene produced, for example, by cracking; ethylene oxide produced, for example, by oxidation of ethylene; monoethylene glycol produced, for example, by hydration of ethylene oxide; ethylene dichloride produced, for example, by chlorination of ethylene; vinyl chloride produced, for example, from ethylene dichloride; alpha-olefins produced, for example, by oligomerization; olefins and diolefins produced, for example, by dehydrogenation of paraffins; isoparaffins produced, for example, by the isomerization of normal paraffins (e.g., isobutane produced from n-butane); aromatics (BTX) produced, for example, from paraffins and/or naphthenes by cyclization and/or dehydrogenation; aromatics produced, for example, from naphtha by cyclization and/or dehydrogenation; aromatics produced, for example by transalkylation or dealkylation, cyclohexane produced, for example, by benzene hydrogenation, ethylbenzene produced, for example, by alkylation of benzene with ethylene; styrene produced, for example, by dehydrogenation of ethyl benzene; cumene produced, for example, by alkylation of benzene with propylene; phenol produced, for example, by oxidation of cumene; terephthalic acid produced, for example, by the oxidation of paraxylene; oxygen produced, for example, by separation from air; nitrogen produced, for example, by separation from air; alcohols produced, for example, by hydroformylation of alkenes, esters produced, for example, by condensation of carboxylic acids and alcohols; MTBE produced, for example, by etherification of isobutylene; polyethylene, polypropylene, polyvinylchloride, polystyrene, polycarbonate, and/or polyethylene terephthalate (PE, PP, PVC, PS, PC, PET) produced, for example, by polymerization. Without limitation, in other specific embodiments, the at least one chemical product comprises acetic acid produced, for example, by methanol carbonylation; vinyl acetate produced, for example, by the reaction of acetic acid with ethylene; propylene produced, for example, by methanol oligomerization (generally known as the methanol-to-olefins process); acrylic acid produced, for example, by oxidation of propylene; methacrolein produced, for example, by oxidation of isobutylene; methyl methacrylate produced, for example, by oxidation of methacrolein; acrylonitrile produced, for example, by ammoxidation of propylene; sulfuric acid produced, for example, by the oxidation of sulfur; nitric acid produced, for example, by the oxidation of ammonia; propylene glycol produced, for example, by the hydration of propylene; one or more nylon precursors selected from adipic acid, caprolactam, cyclohexanone, 1,6 diaminohexane, or a combination thereof; or polyvinyl alcohol (PVA), polyacrylates, polymethylmethacrylate (PMMA), nylons. Without limitation, in specific embodiments, the at least one chemical product comprises a chemical produced, for example, as described in U.S. Provisional Patent Application Nos. 62/792,631, 62/792,632, 62/792,633, 62/792,634, and 62/792,635, entitled *Use of Renewable Energy in the Production of Chemicals*, which are being filed on Jan. 15, 2019, the disclosure of each of which is hereby incorporated herein for purposes not contrary to this disclosure).

This disclosure describes a chemical synthesis plant for producing a chemical product, wherein the chemical synthesis plant is configured/operable such that a majority of the energy required by one or more sections, units, or groups of like units or unit operations of the chemical synthesis plant is provided by non-carbon based energy ($E_{NC}$) from a non-carbon based energy source (e.g., not produced via the combustion of a carbon-based fuel such as a hydrocarbon), from renewable energy (e.g., from non-fossil fuel derived energy ($E_{NF}$)), and/or from electricity, and/or from renewable electricity. The $E_{NC}$ or $E_{NF}$ source may, in embodiments, comprise, primarily comprise, consist, or consist essentially of electricity. The $E_{NC}$ or $E_{NF}$ source may, in embodiments, comprise, primarily comprise, consist, or consist essentially of renewable electricity. In embodiments a portion (e.g., greater than or equal to about 5, 10, 20, 30, 40, 50), a majority (e.g., greater than or equal to about 50, 60, 70, 80, 90, or 95%), or all (e.g., about 100%) of the net energy needed by the overall chemical synthesis plant, a section of the plant (e.g., a feed pretreating section, a reaction section, and/or a product purification section), a group of like units (e.g., compressors, power providing units, heating units, reboilers, refrigeration units, cooling units, separators, reactors, distillation/fractionation columns), or unit operations (e.g., compression, powering, heating and/or cooling operations, reactions, separations) of the plant, or a combination thereof is provided by electricity, renewable energy (e.g., non-fossil fuel derived energy ($E_{NF}$)), or non-carbon based energy ($E_{NC}$). In embodiments, electricity is provided from a renewable energy source, such as, without limitation, wind (e.g., via wind turbines), solar (e.g., photovoltaic (PV) panels or solar thermal), hydroelectric, wave, geothermal, nuclear, tide, biomass combustion with associated capture of $CO_2$ in replacement crops, or a combination thereof. In embodiments a portion (e.g., greater than or equal to about 5, 10, 20, 30, 40, 50), a majority (e.g., greater than or equal to about 50, 60, 70, 80, 90, or 95%), or all (e.g., about 100%) of the electricity, renewable energy (e.g., non-fossil fuel derived energy ($E_{NF}$)), or non-carbon based energy ($E_{NC}$) needed by the overall chemical synthesis plant, a section of the plant (e.g., a feed pretreating section, a reaction section, and/or a product purification section), a unit or a group of like units (e.g., compressors, power providing units, heating units, reboilers, cooling units, refrigeration units, reactors, separators, distillation/fractionation columns) or unit operations (e.g., compressing, powering, separating, heating, cooling, reacting) of the chemical synthesis plant, or a combination thereof, and conventionally provided in a similar chemical synthesis plant via combustion of a fuel, a carbon-based fuel, and/or a fossil fuel and/or the use of steam (e.g., that was itself generated via combustion of a fuel) as an intermediate heat (and/or energy) transfer fluid, is provided without combusting a fuel, a carbon-based fuel, and/or a fossil fuel and/or without use of steam generated by the combustion of such a fuel as an intermediate heat (and/or energy) transfer fluid. In embodiments, the net energy for the overall plant or one or more sections, units or groups of like units of the plant is provided by electricity from a renewable energy source. For example, in embodiments, heating is electrically provided via resistive heating, inductive heating, or otherwise converting electrical energy into thermal and/or mechanical energy.

In embodiments, a chemical synthesis plant of this disclosure is configured such that a majority (e.g., greater than 50, 60, 70, 80, or 90%) of the net energy needed for powering, heating, cooling, compressing, separating, or a combination thereof utilized via the feed pretreating system, one or more reactors, a product purification system, or a combination thereof is provided by electricity.

In embodiments, a chemical synthesis plant according to embodiments of this disclosure is a large plant having a production capacity for the desired chemical product of greater than or equal to about 10,000 tons per year, 100,000 tons per year, 250,000 tons per year, 1,000,000 tons per year, 1,500,000 tons per year, or 10,000,000 tons per year. At the sizes anticipated in this disclosure, the amount of energy provided by a non-carbon based energy source, a renewable energy source and/or electricity will be correspondingly large. In embodiments, a partially or completely electrified plant according to the methods of this disclosure will consume greater than or equal to about 25, 50, 100, 150, 200, 300, 400, 500, 750, or 1000 MW of electricity.

Although a specific embodiment of a chemical synthesis plant will be utilized to describe the electrification of a chemical synthesis plant, as disclosed herein, it is to be understood that numerous arrangements of units and a variety of chemical synthesis technologies can be electrified as per this disclosure, as will be obvious to those of skill in the art upon reading the description herein.

Figure 3:
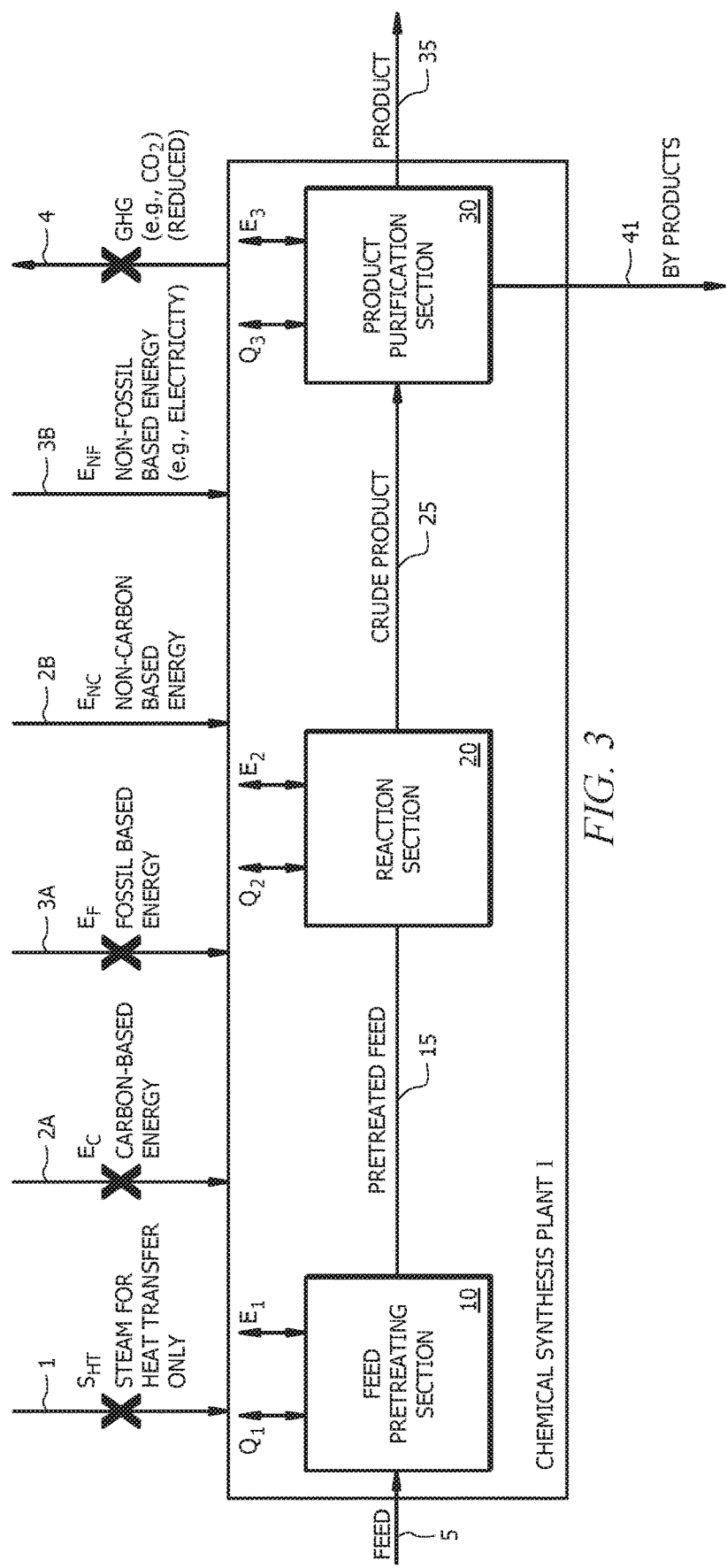
FIG. 3 shows a block flow diagram of a generalized chemical synthesis plant I, according to embodiments of this disclosure.

With reference to FIG. 3, which is an overview of a generalized chemical synthesis plant I, a chemical synthesis plant may be considered to include one or more of the following process sections for converting a feed stream 5 comprising one or more reactants into a chemical product stream 35 (and optionally one or more byproduct streams 41): a feed pretreating section 10, a reaction (or primary reaction) section 20, a product purification section 30, or a combination thereof. Other sections, such as a recycling section, an energy (e.g., electricity) production and/or energy storage (e.g., hydrogen storage) section are also within the scope of this disclosure. Such sections will be described briefly in the next few paragraphs, and in more detail hereinbelow.

As indicated in the chemical synthesis diagram of FIG. 3, a feed pretreating section 10 of a chemical synthesis plant is operable to prepare (e.g., remove undesirable components (e.g., sulfur) from, adjust temperature and/or pressure of a feed) a reactant feed 5 for reaction, providing a pretreated feed 15. In applications, a chemical synthesis plant of this disclosure does not comprise a feed pretreating section. A reaction or "chemical synthesis" section 20 is operable to produce a desired chemical product from the pretreated feed 15 and thus provide a crude chemical product stream 25. A product purification section 30 is operable to separate a purified chemical product 35 from the crude chemical product stream 25. In applications, a chemical synthesis plant of this disclosure does not comprise a product purification section.

As mentioned above and depicted in FIG. 3, energy (E) input to or within the chemical synthesis plant or one or more sections or groups of units, like units, or unit operations thereof (that may conventionally be provided via a carbon based energy ($E_C$) 2A from a carbon based energy source, a fossil fuel derived energy ($E_F$) 3A from a fossil fuel-based energy source, or via the use of steam (e.g., steam generated for this purpose using energy derived from a carbon or fossil fuel based energy source) solely or primarily as a heat or energy transfer medium ($S_{HT}$) 1), may be partially or completely replaced by non-carbon based energy ($E_{NC}$) 2B from a non-carbon based energy source and/or electricity (electricity and/or renewable electricity). The carbon based energy ($E_C$) 2A, the fossil fuel derived energy ($E_F$) 3A, or both can be partially or completely replaced by electricity. The electricity may be derived from a non-carbon based fuel, a renewable fuel, a renewable energy source, or a combination thereof, in embodiments. A benefit derived via the herein disclosed system and method may be a reduction in the greenhouse gas (GHG) emissions 4 from the chemical synthesis plant or process.

Although not intending to be limited by the examples provided herein, a description of some of the ways a chemical synthesis plant can be electrified according to embodiments of this disclosure will now be provided with reference to the exemplary chemical synthesis plant I of FIG. 3. The steps, sections, groups of units or unit operations described may be present or operated in any suitable order, one or more of the steps, sections, units, or unit operations may be absent, duplicated, replaced by a different step, section, unit or unit operation, and additional steps, sections, units or unit operations not described herein may be employed, in various embodiments. Additionally, although a step is noted as being in a particular section, the step could also be considered a part of another section.

As noted hereinabove, in embodiments, a chemical synthesis plant of this disclosure comprises a feed pretreating section 10. Such a feed pretreating section 10 can be operable to remove one or more components such as, without limitation, catalyst poisons, from a feed (or multiple feeds), adjust a pressure of the feed or feeds to a desired operating pressure within a downstream (e.g., reaction) section 20, adjust the temperature of the feed or feeds to a desired operating temperature, and/or otherwise alter a feed or feeds prior to a downstream (e.g., reaction) section 20.

As noted hereinabove, in embodiments, a chemical synthesis plant of this disclosure comprises a chemical synthesis section 20. Such a chemical synthesis section 20 can be operable to produce a desired chemical (or more than one desired chemical) from the feed(s) 5 or the pretreated feed(s) 15. Producing the desired chemical can comprise maintaining one or more reactors at a desired temperature(s)/temperature profile(s) and/or pressure(s), providing additional components (e.g., diluents, catalyst) at a desired composition, temperature and/or pressure, to the one or more reactors, extracting the chemical product from the one or more reactors, and the like, to provide the crude chemical product 25. The one or more reactors can be configured to operate in series or in parallel, and one or more chemical reaction may occur, either in series or in parallel. The reactions occurring may be endothermic, exothermic, or thermoneutral in nature, and the net of all reactions occurring may be endothermic, exothermic, or thermoneutral in nature.

As noted hereinabove, in embodiments, a chemical synthesis plant of this disclosure optionally comprises a product purification section 30. Such a product purification section 30 can be operable to separate a chemical product or multiple products and byproducts from the crude chemical product in any number of ways. For example, separations may be effected via one or more distillation columns and associated reboilers, flash separators, solvent extractors, crystallizers, evaporators, phase separators (e.g., decanters, cyclones, etc.), absorbers, adsorbers, membranes, and the like, to provide the chemical product stream 35.

As indicated in FIG. 3, in embodiments, a majority, greater than 20, 30, 40, 50, 60, 70, 80, or 90%, or substantially all of the net energy needed within the chemical synthesis plant or one or more sections thereof (e.g., the energy E1 needed within the feed pretreating section 10, the energy E2 needed within the reaction section 20, and/or the energy E3 needed within the product purification section 30) [or within one or more units or groups of units (e.g., compressors, separators, distillation columns) or unit operations (e.g., compression, powering, separating, heating, cooling), as discussed hereinbelow] is provided from a non-carbon based energy source, from a renewable energy source, such as renewable electricity, or from electricity (from any source, renewable and/or non-renewable). In embodiments, a majority, greater than 20, 30, 40, 50, 60, 70, 80, or 90%, or substantially all of the net energy (e.g., E=E1+E2+E3) needed within the chemical synthesis plant or one or more sections thereof (e.g., the energy E1 needed within the feed pretreating section 10, the energy E2 needed within the reaction section 20, and/or the energy E3 needed within the product purification section 30) [or within or one or more units or groups of units (e.g., compressors, separators, distillation columns) or unit operations (e.g., compression, powering, separating, heating, cooling), as discussed hereinbelow] is provided without burning a fuel and/or without producing steam solely or at all as a heat (and/or energy) transfer medium.

In embodiments, a majority, greater than 20, 30, 40, 50, 60, 70, 80, or 90%, or substantially all of the net energy needed by one or more units or groups of units or unit operations is provided from a non-carbon based energy source, from a renewable energy source, such as renewable electricity, and/or from electricity (from any source, renewable and/or non-renewable). For example, without limitation, in embodiments, such units comprise compressors (e.g., feed compressors and/or refrigeration compressors), pumps, separators (e.g., distillation columns, absorption units and/or strippers), extractors (e.g., for liquid-liquid extraction), reactors for a particular reaction (e.g., individual reactors or multiple reactors in series and/or in parallel), heaters (e.g., heat exchangers and/or reboilers), coolers (e.g., refrigeration units and/or cryogenic units, blowers, cooling water systems), equipment for regeneration (e.g., for the regeneration of catalysts, adsorbers, or stripping solutions), or combinations thereof.

In embodiments, a majority, greater than 20, 30, 40, 50, 60, 70, 80, or 90%, or substantially all of the net energy needed for a set of operations (e.g., compression, pumping, powering, mixing, separating, heating, cooling, reacting, recycling, energy storing and/or energy producing) is provided from a non-carbon based energy source, from a renewable energy source, such as renewable electricity, of from electricity (from any source, renewable and/or non-renewable).

A significant fraction of the energy (E) used in chemical plants is used for heating and cooling (Q); because of its importance, the fraction of all net energy transferred as heating and cooling can be considered separately. As noted above, in embodiments, a majority, greater than 20, 30, 40, 50, 60, 70, 80, or 90%, or substantially all of the net energy needed for heating and/or cooling is provided from a non-carbon based energy source, from a renewable energy source, such as renewable electricity, and/or from electricity (from any source, renewable and/or non-renewable). For example, in embodiments, a majority, greater than 20, 30, 40, 50, 60, 70, 80, or 90%, or substantially all of the net heat input or removal needed within the chemical synthesis plant or one or more sections thereof (e.g., the heat input or removal Q1 needed within the feed pretreating section 10, the heat input or removal Q2 needed within the reaction section 20, and/or the heat input or removal Q3 needed within the product purification section 30) and provided by one or more units or groups of units (e.g., refrigeration units, heat exchangers) is provided from a non-carbon based energy source, from a renewable energy source, such as renewable electricity, and/or from electricity (from any source, renewable and/or non-renewable). According to this disclosure, when cooling process streams, as much heat as possible can be used to heat other process streams. However, below a certain temperature, further heat transfer is no longer effective or useful, and blowers, cooling water, and/or refrigeration (which require an energy input for heat removal) are utilized. In embodiments, for example, heat exchangers, refrigeration units, or a combination thereof for altering the temperature of process streams may be powered electrically. In embodiments, refrigeration units contain one or more electrically-powered compressors. In embodiments, steam is not utilized solely as an intermediate heat and/or energy transfer stream, and the plant or section(s) thereof do not comprise an elaborate steam system such as conventionally employed for energy transfer. In embodiments, steam is used as a heat transfer fluid and is not used to do mechanical work, for example to drive a pump or compressor. In embodiments, heating is provided via resistive heating. In embodiments, heating is provided via inductive heating. In embodiments, heating is provided electrically to radiative panels that then transfer heat to the process by radiation. The above-noted elimination or reduction of the steam system may also result in lower capital and operating costs, in embodiments.

Reactors of the reaction section 20 or elsewhere which may, in embodiments, conventionally be heated either directly or indirectly via the burning of a fuel may, according to embodiments of this disclosure, be heated without burning a fuel (and, thus, without the concomitant production of corresponding flue gas). For example, reactor(s) can, in embodiments, be electrically heated. In this manner, greenhouse gas emissions from a plant can be reduced and, in some instances, hydrocarbons conventionally burned as a fuel within the reaction section 20 (or elsewhere) can be utilized in the production of additional chemical product either within that plant or in a different chemical production plant. In embodiments, energy efficiency is increased by the elimination of the flue gas, since the loss of heat contained in the flue gas to the atmosphere is eliminated. Utilization of electrical heating of reactors can, in embodiments, provide for an enhanced temperature profile along a reaction zone or reactor. For example, a desired heat flux may be provided along a length of a reactor, providing enhanced temperature control for reaction, shifting equilibrium, and/or minimizing coking and/or catalyst deactivation.

In embodiments, one or more reactors, a feed preparation system, a product purification system, or a combination thereof produces a lights stream (e.g., a flue gas, purge gas, or tailgas), wherein the lights stream, the reactants utilized in the one or more reactors, or a combination thereof comprise a component selected from hydrogen, carbon monoxide, one or more light hydrocarbon (e.g., a $C_1$ hydrocarbon, $C_2$ hydrocarbon, $C_3$ hydrocarbon, and/or a $C_4$ hydrocarbon), or a combination thereof, and a chemical synthesis plant of this disclosure is not configured for combustion of the lights stream, the component, or both as a fuel. In embodiments, the energy of such combustion is replaced by electricity. In embodiments, the purge gas is sold and/or used as a feed to produce other chemicals, or the purge gas is separated into two or more streams of which at least one can be sold or used to produce other chemicals.

In embodiments, electricity can be utilized to produce colder cooling water (e.g., 2, 5, 10 or 15° C. colder) than conventional, enhancing downstream operations. In embodiments, electrical power can be used in operations to improve the quality of water to be used for cooling water, e.g., by removing contaminants. In embodiments, electricity can be used to heat gas or liquid streams used to regenerate a catalyst, adsorbent, or absorption solution, for example steam stripping of an adsorbent to regenerate it. In embodiments, electricity is used to regenerate an amine absorption solution. In embodiments, electricity can be used to preheat gases used in reactions. In embodiments, electricity can be used to vaporize feeds and/or diluents, for example steam or naphtha. In embodiments, electricity can be used to heat trace lines or vessels and keep gases and/or liquids at a desired temperature during storage and/or transfer when they would otherwise cool off. In embodiments, electricity can be used to power a thermoelectric device and/or a heat pump to enable simultaneous heating and cooling. In embodiments, electricity is used to power a heat pump that is used to distribute and/or remove heat. In embodiments, heat is transferred by means of a vapor compression heat pumping system. In embodiments, an organic Rankine cycle is used as an energy carrying mechanism. In embodiments, electricity can be used to provide "trim heating," wherein a gas or liquid stream, previously heated by heat transfer from a hot reaction product stream (via a feed/product interchanger), is further heated prior to feeding said stream to a reactor or other downstream apparatus. In embodiments, electricity can be used to provide "start-up" heating to a process, wherein an electrically powered heater may be used to preheat a reactant or other process stream when a plant is started-up but is no longer utilized when the plant is on line, as other heat sources, such as without limitation hot reactor product streams, become available.

As noted above, in embodiments, a majority, greater than 20, 30, 40, 50, 60, 70, 80, or 90%, or substantially all of the energy needed for compression within the chemical synthesis plant or one or more sections thereof (e.g., the feed pretreating section 10, the reaction section 20, and/or the product purification section 30) is provided from a non-carbon based energy source, from a renewable energy source, such as renewable electricity, and/or from electricity (from any source, renewable and/or non-renewable). Such compression may be utilized, for example, to raise the pressure of the feed 5 in pretreating section 10, to raise the pressure of a stream within the reaction section 20, to raise the pressure of a stream within the product purification section 30, and/or to raise the pressure of a recycle stream.

For example, according to embodiments of this disclosure, compression may be effected via electric motor-driven compressors, rather than via turbines driven by the combustion of a gas/fuel or via turbines powered by steam produced from the combustion of hydrocarbons. In embodiments, compressors are operated with turbines driven by steam produced with electric heating. For example, an electric motor and/or a turbine driven by steam produced electrically may be utilized to provide compression throughout the chemical synthesis plant or one or more sections thereof, or for one or more operations (e.g., refrigeration). In embodiments, a majority, greater than 20, 30, 40, 50, 60, 70, 80, or 90%, or substantially all of the compressors within one or more sections of the chemical plant or a group of like units (e.g., refrigeration units) or operations (e.g., stream pressurizing, cooling, refrigerating) utilize an electric motor-driven compressor and/or a turbine driven by electrically produced steam.

In embodiments, high pressure streams within the plant are utilized to produce electricity for use within one or more sections of the chemical synthesis plant. For example, pressure let down steps within the chemical synthesis plant or one or more sections thereof may be effected via turbine(s) rather than control valves, in embodiments.

In embodiments, steam generated by the combustion of fuels or produced solely for heat and/or energy transfer is not utilized in a chemical synthesis plant and method of this disclosure (e.g., in the pretreating section 10, the reaction section 20, and/or the product purification section 30). In this manner, a chemical synthesis plant according to this disclosure can be operated, in embodiments, without an elaborate steam heat and/or energy transfer system (which may be conventionally utilized in a chemical plant for producing the same chemical). In some applications, for example where steam is utilized within a reactor as a feed component and/or diluent, such steam may be produced via heat transfer with a process stream within the chemical synthesis plant and/or may be produced electrically. In embodiments, steam generated via heat transfer with a process stream may be superheated using electricity. In embodiments, the electrical superheating of low temperature steam allows for improved heat and energy recovery. In embodiments, steam is not utilized throughout the chemical synthesis plant as a commodity or utility. In embodiments, a chemical synthesis plant of this disclosure is essentially steam-free, or utilizes substantially less steam (e.g., uses at least 10, 20, 30, 40, 50, 60, 70, 80, 90, or 100 volume percent (vol %) less steam) than a conventional plant for producing the same chemical. For example, a conventional plant for producing the same chemical may utilize steam production for reboilers of distillation columns of the feed pretreating section 10 and/or the product purification section 30, may utilize steam production to drive steam turbines for compressing process and/or recycle streams, or may utilize steam production to drive steam turbines for refrigeration. In embodiments, steam is not produced for these operations in a chemical plant according to this disclosure, or substantially less steam is produced (e.g., at least 10, 20, 30, 40, 50, 60, 70, 80, 90, or 100 volume percent (vol %) less steam). In embodiments, steam is used as a heat transfer fluid, but is not used to do mechanical work (e.g., to drive a compressor or pump.) In embodiments, the steam generated for these operations is primarily (e.g., of the total steam utilized, the greatest percentage is electrically produced), mainly (e.g., greater than 50% of the steam is electrically produced) or substantially all electrically produced. In embodiments, the steam utilized as a reactant or diluent is primarily (e.g., of the total steam utilized, the greatest percentage is electrically produced), mainly (e.g., greater than 50% of the steam is electrically produced) or substantially all electrically produced. In embodiments, the steam utilized as a reactant or diluent is generated using resistive heating. In embodiments, the steam utilized as a reactant or a diluent is generated using an electrode boiler or an immersion heater. In embodiments, steam is superheated using electricity.

In embodiments, in a chemical synthesis plant or process of this disclosure, more energy is utilized directly 'as-is', for example, utilizing heat from a hot product effluent stream to heat a feed stream, rather than being transformed, e.g., via the generation of steam and the conversion of the thermal energy to mechanical energy via a steam turbine. According to embodiments of this disclosure, the use of energy directly can increase the energy efficiency of the chemical synthesis plant, for example by reducing energy efficiency losses that occur when heat is converted to mechanical energy.

In embodiments, electricity can be used to provide the motive force for fluids. For example, electricity can be used to power pumps to move and/or pressurize liquids, and/or to power air blowers and/or fans. In embodiments, a fraction, a majority, or all (e.g., 20, 30, 40, 50, 60, 70, 80, 90, or 100%) of the number of pumps utilized in the chemical synthesis plant are electrified.

As noted above, in embodiments, a majority, greater than 20, 30, 40, 50, 60, 70, 80, or 90%, or substantially all of the energy needed for separating/separations is provided from a non-carbon based energy source, from a renewable energy source, such as renewable electricity, of from electricity (from any source, renewable and/or non-renewable). A variety of separations can be effected electrically, as per embodiments of this disclosure. Separations based on temperature and/or pressure change can include heating/cooling and/or compressing electrically, as described above. For example, distillations, gas/solid separations, absorption, stripping, solvent extraction, extractive distillation, pressure swing adsorption, temperature swing adsorption, flash separation, crystallization or a combination thereof may be electrified in embodiments of this disclosure. By way of non-limiting example, distillation columns of one or more sections of the plant can be electrically heated, in embodiments. In embodiments, reboilers associated with a distillation column are electrically heated and/or are heated via steam (or another fluid) produced electrically. In embodiments, reboilers associated with a distillation column are heated with an electric immersion heater. In embodiments, electricity is used to power a thermoelectric device or a heat pump to provide both heating (to the reboiler) and cooling (to the condenser) in a distillation column. In embodiments, steam for use in stripping is generated electrically.

As noted above, when utilizing electricity from a renewable source that has a potentially or known intermittent supply (e.g., an intermittent energy source or IES), various steps can be taken to maintain operation of the chemical synthesis plant, according to embodiments of this disclosure. Such handling of an IES can be as described in U.S. Provisional Patent Application Nos. 62/792,636 and 62/792,637, entitled *Use of Intermittent Energy in the Production of Chemicals*, which are being filed on Jan. 15, 2019, the disclosure of each of which is hereby incorporated herein for purposes not contrary to this disclosure. For example, in embodiments, compressed hydrogen is stored for intermittency of electric supply. Alternatively or additionally, one or more cryogenic liquids can be stored for intermittency of electric supply. Alternatively or additionally, heat can be stored for intermittency of electric supply. Alternatively or additionally, batteries can be kept for intermittency of electric supply. Backup power for key components may be provided; in embodiments, non-renewable electricity may be utilized as a back-up for intermittent renewable electricity. For example, such backup power may be produced via apparatus driven by compressed gas or a flywheel.

In embodiments, gaseous feeds and/or products are compressed and stored for intermittency of electric supply. In embodiments, gaseous feeds and/or products are compressed and stored at a pressure greater than the process operating pressure, and when the pressure is reduced, electricity is generated. In embodiments, gaseous feeds and/or products are compressed and liquefied when electricity is readily available, and vaporized and expanded to generate electricity and/or to provide feed when electricity is not readily available. In embodiments, feeds or products are chilled and stored for use as a refrigerant for intermittency of electric supply. For example, propane or ammonia can, in embodiments, be chilled when electricity is readily available and used to cool streams when electricity is not available; the resulting warmer liquid or gas can then be utilized as a feed and/or withdrawn as a product. In embodiments, hydrogen is stored and later passed through a fuel cell to generate electricity to handle intermittency of electric supply. In embodiments, hydrogen generated within the process (e.g., separated from a purge stream) is stored for later use to generate electricity or steam. In embodiments, oxygen or nitrogen generated in an air separation plant is stored under pressure for later use, possibly with electricity generation via expansion. In embodiments, thermal energy may be stored using phase change materials wherein thermal energy may be captured (e.g., from a process stream or renewable energy) as the latent heat of liquefaction by melting the material. The energy is recovered by bringing a process stream in thermal contact, directly or indirectly, with the phase change material and allowing the material to solidify. Through appropriate selection of the phase change material thermal energy may be stored at any desired temperature. In embodiments, the phase change material may provide process heating at the same temperature as the phase change. For example, sodium nitrite, which has a melting point of approximately 271° C., can be utilized, in embodiments, as a phase change material to store and liberate thermal energy at a temperature suitable for preheating a gas stream comprising CO and $H_2$ to an appropriate temperature for feeding to a methanol synthesis reactor. Alternatively, boron oxide, which has a melting point of approximately 450° C., can be utilized, in embodiments, as a phase change material to store and liberate thermal energy at a temperature suitable for preheating a gas stream comprising $N_2$ and $H_2$ to an appropriate temperature for feeding to an ammonia synthesis reactor. In embodiments of such applications the phase change material may be melted using electrical heaters or by extracting some heat present in a process stream whenever the IES is available.

Duplicate apparatus or apparatus capable of using multiple energy sources may be utilized, in embodiments, to handle IES. For example, compressors driven by steam or gas turbines may be provided as a backup for electric motor-driven compressors. In embodiments, non-renewable electricity can be utilized as a back-up for intermittent renewable electricity, for example, to power electric motor-driven compressors.

Electrification of the chemical synthesis plant of this disclosure can be provided via an electricity supply that can be high voltage or low voltage. The electric devices can be operable or operated on alternating (single or multiphase) or direct current.

As energy consumption (e.g., to maintain desired temperatures and pressures) represents a large percent of the operating cost for a traditional chemical synthesis plant, increasing energy efficiency (e.g., via electrification) as per this disclosure and/or utilizing one or more components conventionally burned to provide heat and/or burned for compression (e.g., burned in a reactor to maintain a desired operating temperature, burned to produce steam for a steam turbine, and/or burned for a gas turbine) to produce additional chemical product may provide economic advantages over a conventional chemical synthesis plant. In embodiments, the energy efficiency provided by the chemical synthesis plant can be increased by at least 5, 10, 20, 30, 40, 50, 60, or 70% relative to the conventional chemical production system. In embodiments, the amount of hydrocarbon burned for fuel is reduced by 10, 20, 30, 40, 50, 60, 70, 80, 90, 95, or 100% relative to an otherwise similar conventional chemical plant. In embodiments, aspects of this disclosure (e.g., the elimination of the costly steam system) can serve to reduce the large investment cost required to construct a new chemical facility. Concomitantly, the reduction of the burning of fossil fuels (e.g., natural gas, methane) as a fuel enabled via this disclosure provides for reduced greenhouse gas (GHG) emissions relative to a conventional chemical synthesis plant in which hydrocarbons are burned as fuel. In embodiments, GHG emissions (e.g., carbon dioxide emissions) are reduced by at least 5, 10, 20, 25, 30, 40, 50, 60, 70, 80, 90, 95%, 98%, or 100% relative to a conventional chemical synthesis plant in which hydrocarbons are burned as fuel. In embodiments, aspects of this disclosure can lead to an increase in carbon efficiency of a process, i.e. to a fraction of carbon consumed in the process that reappears as a useful product, and/or a reduced specific energy consumption (e.g., the energy utilized to synthesize a quantity of chemical product). In embodiments, the specific energy consumption (e.g., the net external energy supplied to the process divided by the amount of product produced) is decreased over an otherwise similar conventional process by 10, 20, 30, 40, 50, 60, or 70%. In embodiments, the carbon efficiency of a process (e.g., the fraction of the carbon in the feed and fuel that appears in the final product) is increased by 2, 3, 4, 5, 10, 15, 20, 25, 30, or 35% relative to an otherwise similar conventional process.

Conventionally, the energy required for unit operations in chemical processes is generally provided by the burning of fossil fuels, especially natural gas. Herein-disclosed are systems and methods by which this energy input can be reduced or replaced with non-carbon based energy, renewable energy, such as renewable electricity, and/or by electricity from any source (e.g., renewable and/or non-renewable), such that energy efficiency is improved (e.g., energy losses are reduced). In embodiments, energy efficiency (e.g., reduced energy losses) is increased by a decrease in or elimination of the use of steam to do mechanical work. The herein-disclosed use of non-carbon based energy, renewable energy, and/or electricity in the production of chemicals can increase energy efficiency of and decrease carbon dioxide emissions from and fossil energy consumption within the chemical synthesis process, and may provide additional feed by reducing or eliminating the burning of a feed component as a fuel.

While various embodiments have been shown and described, modifications thereof can be made by one skilled in the art without departing from the spirit and teachings of the disclosure. The embodiments described herein are exemplary only, and are not intended to be limiting. Many variations and modifications of the subject matter disclosed herein are possible and are within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_L$ and an upper limit, $R_U$ is disclosed, any number falling within the range is specifically disclosed. In particular, the following numbers within the range are specifically disclosed: $R=R_L+k*(R_U-R_L)$, wherein k is a variable ranging from 1 percent to 100 percent with a 1 percent increment, i.e., k is 1 percent, 2 percent, 3 percent, 4 percent, 5 percent, . . . 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present disclosure. Thus, the claims are a further description and are an addition to the embodiments of the present disclosure. The discussion of a reference is not an admission that it is prior art to the present disclosure, especially any reference that may have a publication date after the priority date of this application. The disclosures of all patents, patent applications, and publications cited herein are hereby incorporated by reference, to the extent that they provide exemplary, procedural, or other details supplementary to those set forth herein.

Additional Disclosure Part I

The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. Alternative embodiments that result from combining, integrating, and/or omitting features of the embodiment(s) are also within the scope of the disclosure. While compositions and methods are described in broader terms of "having", "comprising," "containing," or "including" various components or steps, the compositions and methods can also "consist essentially of" or "consist of" the various components and steps. Use of the term "optionally" with respect to any element of a claim means that the element is required, or alternatively, the element is not required, both alternatives being within the scope of the claim.

Numbers and ranges disclosed above may vary by some amount. Whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an", as used in the claims, are defined herein to mean one or more than one of the element that it introduces. If there is any conflict in the usages of a word or term in this specification and one or more patent or other documents, the definitions that are consistent with this specification should be adopted.

Embodiments disclosed herein include:

A: A chemical synthesis plant comprising: one or more reactors configured for producing, from one or more reactants, a process stream comprising at least one chemical product; a feed preparation system configured to prepare one or more feed streams comprising one or more of the one or more reactants for introduction into the one or more reactors; and/or a product purification system configured to separate the at least one chemical product from reaction byproducts, unreacted reactants, or a combination thereof within the process stream, wherein the chemical synthesis plant is configured such that a majority (e.g., greater than 50, 60, 70, 80, 90, or 100%) of the net energy needed for heating, cooling, compressing, or a combination thereof utilized via the one or more reactors, the feed preparation system, the product purification system, or a combination thereof is provided from a non-carbon based energy source, from a renewable energy source, and/or from electricity.

B: A chemical synthesis plant wherein a majority (e.g., greater than 50, 60, 70, 80, 90, or 100%) of the net energy input conventionally provided by the combustion of a fuel is provided by electricity.

C: A chemical synthesis plant wherein a majority of the net energy conventionally provided by the combustion of a fuel is provided by a non-carbon based energy source, a renewable energy source, and/or renewable electricity.

D: A chemical synthesis plant comprising: one or more reactors configured for producing, from one or more reactants, a process stream comprising at least one chemical product; a feed preparation system configured to prepare one or more feed streams comprising one or more of the one or more reactants for introduction into the reactor; and/or a product purification system configured to separate the at least one chemical product from reaction byproducts, unreacted reactants, or a combination thereof within the process stream, wherein the chemical synthesis plant is configured: (a) such that no combustion flue gas is produced; (b) without a substantially plant-wide steam system; (c) such that no steam is utilized therein to perform mechanical work; (d) such that any steam utilized as a diluent and/or reactant within the chemical synthesis plant is generated with electricity; (e) such that any steam utilized as a diluent and/or a reactant is superheated electrically to provide heat/raise the temperature of a process stream; (f) such that heat obtained from cooling process streams is utilized solely to preheat other process streams; or (g) any combination of (a)-(f).

Each of embodiments A, B, C, and D may have one or more of the following additional elements: Element 1: wherein conventional chemical synthesis plants for producing the same chemical product are configured such that less of the net energy needed by the conventional chemical synthesis plant is provided by a non-carbon based energy source, from a renewable energy source, and/or from electricity. Element 2: wherein the electricity comprises partially, primarily, or substantially entirely electricity from a renewable source. Element 3: wherein the renewable source comprises solar, wind, geothermal, hydroelectric, wave, tidal, nuclear or a combination thereof. Element 4: wherein the net energy needed for heating, cooling, compression, or a combination thereof utilized via the one or more reactors, the feed preparation system, the product purification system, or a combination thereof is not provided by combustion. Element 5: wherein, relative to an otherwise similar chemical synthesis plant that is configured for combustion of at least a portion of a byproduct or product stream as a fuel, the chemical synthesis plant produces reduced emissions (e.g., of greenhouse gases, carbon dioxide ($CO_2$), flare gas, nitrogen oxides, sulfur oxides, etc.). Element 6: wherein: (a) steam is not intentionally produced solely for the purpose of heat and/or energy transfer; (b) steam is not used as a primary or is not used at all as a heat and/or energy transfer medium; (c) steam is used only to facilitate the transfer of heat from one process stream to another; (d) steam is not utilized for mechanical work; or (e) all intentionally produced steam is generated electrically. Element 7: wherein the one or more reactors, the feed preparation system, the product purification system, or a combination thereof produces a lights stream (e.g., a flue gas, purge gas, or tailgas), wherein the lights stream, the reactants, or both comprise a component selected from hydrogen, carbon monoxide, one or more light hydrocarbon (e.g., a $C_1$ hydrocarbon, $C_2$ hydrocarbon, $C_3$ hydrocarbon, and/or a $C_4$ hydrocarbon), or a combination thereof, and wherein the chemical synthesis plant is not configured for combustion of the lights stream, the component, or both as a fuel, and optionally where the energy of combustion is replaced by electricity. Element 8: wherein the lights stream is a stream that is conventionally combusted as a fuel and/or flared. Element 9: wherein the chemical synthesis plant further comprises a recycle line whereby the component, the lights stream, or both can be reintroduced, either directly or following further processing and/or purification, into at least one of the one or more reactors as a reactant. Element 10: wherein the component is a reactant, and wherein configuration of the chemical synthesis plant without combustion of the component provides, relative to a conventional chemical synthesis plant for producing the at least one chemical product, an additional amount of the component to be converted into the at least one chemical product within the one or more reactors. Element 11: wherein the at least one component comprises methane. Element 12: wherein: the at least one chemical product comprises ethylene, and the one or more reactors comprise one or more steam crackers; the at least one chemical product comprises ammonia, and the one or more reactors comprise one or more ammonia synthesis reactors; or the at least one chemical product comprises methanol, and the one or more reactors comprise one or more methanol synthesis reactors. Element 13: wherein the chemical synthesis plant is configured for the production of: propylene by cracking; ethylene oxide by oxidation of ethylene; monoethylene glycol by hydration of ethylene oxide; ethylene dichloride by chlorination of ethylene; vinyl chloride from ethylene dichloride; alpha-olefins by oligomerization; olefins and/or diolefins by dehydrogenation of paraffins; isoparaffins by isomerization of normal paraffins; aromatics (BTX) from paraffins and/or naphthenes by cyclization and/or dehydrogenation; aromatics from naphtha by cyclization and/or dehydrogenation; ethylbenzene by alkylation of benzene with ethylene; styrene by dehydrogenation of ethyl benzene; cumene by alkylation of benzene with propylene; phenol by oxidation of cumene; terephthalic acid by the oxidation of paraxylene; oxygen by separation from air; nitrogen by separation from air; MTBE by etherification of isobutylene; and/or polyethylene, polypropylene, polyvinylchloride, polystyrene, polycarbonate, or polyethylene terephthalate (PE, PP, PVC, PS, PC, PET) by polymerization. Element 14: wherein the chemical synthesis plant is configured for the production of: acetic acid by methanol carbonylation; vinyl acetate by the reaction of acetic acid with ethylene; propylene by methanol oligomerization (generally known as the methanol-to-olefins process); aromatics by transalkylation or dealkylation; cyclohexane by hydrogenation of benzene; acrylic acid by oxidation of propylene; methacrolein by oxidation of isobutylene; methyl methacrylate by oxidation of methacrolein; acrylonitrile by ammoxidation of propylene; sulfuric acid by the oxidation of sulfur; nitric acid by the oxidation of ammonia; propylene glycol by the hydration of propylene; alcohols by hydroformylation of alkenes; esters, by condensation of carboxylic acids and alcohols; one or more nylon precursors selected from adipic acid, caprolactam, cyclohexanone, 1,6 diaminohexane, or a combination thereof; and/or polyvinyl alcohol (PVA), polyacrylates, polymethylmethacrylate (PMMA), nylons. Element 15: wherein a minority of or substantially none of the electricity is produced either directly or indirectly via combustion (i.e., via chemical energy). Element 16: comprising no gas-fired turbines or steam driven turbines wherein the steam is produced via combustion of a fuel. Element 17: further comprising: one or more electrically powered and/or electrically operated components selected from: thermoelectric devices operable to convert heat flux into electrical energy; heat pumps operable to transfer heat energy from a heat source to a heat sink; distillation columns; flywheels configured to store mechanical energy; heaters. Element 18: further comprising one or more feed or process streams that are vaporized electrically. Element 19: further comprising an electrode boiler or an immersion heater to effect the vaporization. Element 20: wherein the one or more feed or process streams comprise water. Element 21: further comprising stored energy in the form of compressed hydrogen, compressed hydrocarbon(s) of the feed, compressed hydrocarbon products, cryogenic liquids, thermal batteries, electric batteries, phase change materials, or a combination thereof, such that the stored energy from the compressed hydrogen, the compressed hydrocarbon(s) from the feed, the compressed hydrocarbon products, the cryogenic liquids, the thermal batteries, the electric batteries, or the combination thereof can be utilized when renewable electricity is not available or economical. Element 22: further comprising a blower, cooling water, and/or a refrigeration system to effect the at least a portion of the cooling. Element 23: wherein the refrigeration system contains one or more electrically-driven compressors. Element 24: wherein a majority of a number of compressors utilized for the compressors are powered electrically. Element 25: configured such that a majority of the energy for pumping process and/or utility fluids is supplied electrically. Element 26: wherein the amount of hydrocarbon fuel consumed is decreased by at least 10% relative to that of an otherwise similar conventional chemical plant. Element 27: wherein the amount of $CO_2$ produced per ton of product is decreased by at least 10% relative to that of an otherwise similar conventional chemical plant. Element 28: wherein the specific energy consumption is decreased by at least 10% relative to that of an otherwise similar conventional chemical plant. Element 29: wherein the carbon efficiency is increased by at least 5% relative to that of an otherwise similar conventional chemical plant. Element 30: wherein: (a) steam is not intentionally produced solely for the purpose of heat and/or energy transfer; (b) steam is not used as a primary or is not used at all as a heat and/or energy transfer medium; (c) steam is used only to facilitate the transfer of heat from one process stream to another; (d)

steam is not utilized for mechanical work; or (e) all intentionally produced steam is generated electrically. Element 31: wherein the majority of the net energy is provided primarily by electricity from a renewable source.

Additional Disclosure Part II

The following are non-limiting, specific embodiments in accordance with the present disclosure:

A first embodiment, which is a chemical synthesis plant comprising one or more reactors configured for producing, from one or more reactants, a process stream comprising at least one chemical product, a feed preparation system configured to prepare one or more feed streams comprising one or more of the one or more reactants for introduction into the one or more reactors; and/or a product purification system configured to separate the at least one chemical product from reaction byproducts, unreacted reactants, or a combination thereof within the process stream, wherein the chemical synthesis plant is configured such that a majority (e.g., greater than 50, 60, 70, 80, 90, or 100%) of the net energy needed for heating, cooling, compressing, or a combination thereof utilized via the one or more reactors, the feed preparation system, the product purification system, or a combination thereof is provided from a non-carbon based energy source, from a renewable energy source, and/or from electricity.

A second embodiment, which is the chemical synthesis plant of the first embodiment, wherein conventional chemical synthesis plants for producing the same chemical product are configured such that less of the net energy needed by the conventional chemical synthesis plant is provided by a non-carbon based energy source, from a renewable energy source, and/or from electricity.

A third embodiment, which is the chemical synthesis plant of the first embodiment, wherein the electricity comprises partially, primarily, or substantially entirely electricity from a renewable source.

A fourth embodiment, which is the chemical synthesis plant of the third embodiment, wherein the renewable source comprises solar, wind, geothermal, hydroelectric, wave, tidal, nuclear or a combination thereof.

A fifth embodiment, which is the chemical production system of the third embodiment, wherein the net energy needed for heating, cooling, compression, or a combination thereof utilized via the one or more reactors, the feed preparation system, the product purification system, or a combination thereof is not provided by combustion.

A sixth embodiment, which is the chemical synthesis plant of the first or the third embodiment, wherein, relative to an otherwise similar chemical synthesis plant that is configured for combustion of at least a portion of a byproduct or product stream as a fuel, the chemical synthesis plant produces reduced emissions (e.g., of greenhouse gases, carbon dioxide ($CO_2$), flare gas, nitrogen oxides, sulfur oxides, etc.).

A seventh embodiment, which is the chemical synthesis plant of the first or the third embodiment, wherein (a) steam is not intentionally produced solely for the purpose of heat and/or energy transfer; (b) steam is not used as a primary or is not used at all as a heat and/or energy transfer medium; (c) steam is used only to facilitate the transfer of heat from one process stream to another; (d) steam is not utilized for mechanical work; or (e) all intentionally produced steam is generated electrically.

An eighth embodiment, which is the chemical synthesis plant of the first or the third embodiment, wherein the one or more reactors, the feed preparation system, the product purification system, or a combination thereof produces a lights stream (e.g., a flue gas, purge gas, or tailgas), wherein the lights stream, the reactants, or both comprise a component selected from hydrogen, carbon monoxide, one or more light hydrocarbon (e.g., a $C_1$ hydrocarbon, $C_2$ hydrocarbon, $C_3$ hydrocarbon, and/or a $C_4$ hydrocarbon), or a combination thereof, and wherein the chemical synthesis plant is not configured for combustion of the lights stream, the component, or both as a fuel, and optionally where the energy of combustion is replaced by electricity.

A ninth embodiment, which is the chemical synthesis plant of the eighth embodiment, wherein the lights stream is a stream that is conventionally combusted as a fuel and/or flared.

A tenth embodiment, which is the chemical synthesis plant of the ninth embodiment, wherein the chemical synthesis plant further comprises a recycle line whereby the component, the lights stream, or both can be reintroduced, either directly or following further processing and/or purification, into at least one of the one or more reactors as a reactant.

An eleventh embodiment, which is the chemical synthesis plant of the seventh embodiment, wherein the component is a reactant, and wherein configuration of the chemical synthesis plant without combustion of the component provides, relative to a conventional chemical synthesis plant for producing the at least one chemical product, an additional amount of the component to be converted into the at least one chemical product within the one or more reactors.

A twelfth embodiment, which is the chemical synthesis plant of the seventh embodiment, wherein the at least one component comprises methane.

A thirteenth embodiment, which is the chemical synthesis plant of the first or the third embodiment, wherein the at least one chemical product comprises ethylene, and the one or more reactors comprise one or more steam crackers, the at least one chemical product comprises ammonia, and the one or more reactors comprise one or more ammonia synthesis reactors; or the at least one chemical product comprises methanol, and the one or more reactors comprise one or more methanol synthesis reactors.

A fourteenth embodiment, which is the chemical synthesis plant of the first or the third embodiment, wherein the chemical synthesis plant is configured for the production of propylene by cracking, ethylene oxide by oxidation of ethylene, monoethylene glycol by hydration of ethylene oxide, ethylene dichloride by chlorination of ethylene, vinyl chloride from ethylene dichloride, alpha-olefins by oligomerization, olefins and/or diolefins by dehydrogenation of paraffins, isoparaffins by isomerization of normal paraffins, aromatics (BTX) from paraffins and/or naphthenes by cyclization and/or dehydrogenation, aromatics from naphtha by cyclization and/or dehydrogenation, ethylbenzene by alkylation of benzene with ethylene, styrene by dehydrogenation of ethyl benzene, cumene by alkylation of benzene with propylene, phenol by oxidation of cumene, terephthalic acid by the oxidation of paraxylene, oxygen by separation from air, nitrogen by separation from air, MTBE by etherification of isobutylene; and/or polyethylene, polypropylene, polyvinylchloride, polystyrene, polycarbonate, or polyethylene terephthalate (PE, PP, PVC, PS, PC, PET) by polymerization.

A fifteenth embodiment, which is the chemical synthesis plant of the first or the third embodiment, wherein the chemical synthesis plant is configured for the production of acetic acid by methanol carbonylation, vinyl acetate by the reaction of acetic acid with ethylene, propylene by methanol oligomerization (generally known as the methanol-to-olefins process), aromatics by transalkylation or dealkylation, cyclohexane by hydrogenation of benzene, acrylic acid by oxidation of propylene, methacrolein by oxidation of isobutylene, methyl methacrylate by oxidation of methacrolein, acrylonitrile by ammoxidation of propylene, sulfuric acid by the oxidation of sulfur, nitric acid by the oxidation of ammonia, propylene glycol by the hydration of propylene, alcohols by hydroformylation of alkenes, esters, by condensation of carboxylic acids and alcohols, one or more nylon precursors selected from adipic acid, caprolactam, cyclohexanone, 1,6 diaminohexane, or a combination thereof; and/or polyvinyl alcohol (PVA), polyacrylates, polymethylmethacrylate (PMMA), nylons.

A sixteenth embodiment, which is the chemical synthesis plant of the first or the third embodiment, wherein a minority of or substantially none of the electricity is produced either directly or indirectly via combustion (i.e., via chemical energy).

A seventeenth embodiment, which is the chemical synthesis plant of the first or the third embodiment comprising no gas-fired turbines or steam driven turbines wherein the steam is produced via combustion of a fuel.

An eighteenth embodiment, which is the chemical synthesis plant of the first or the third embodiment further comprising one or more electrically powered and/or electrically operated components selected from thermoelectric devices operable to convert heat flux into electrical energy, heat pumps operable to transfer heat energy from a heat source to a heat sink, distillation columns, flywheels configured to store mechanical energy, heaters.

A nineteenth embodiment, which is the e chemical synthesis plant of the first or the third embodiment further comprising one or more feed or process streams that are vaporized electrically.

A twentieth embodiment, which is the chemical synthesis plant of the nineteenth embodiment further comprising an electrode boiler or an immersion heater to effect the vaporization.

A twenty-first embodiment, which is the chemical synthesis plant of the nineteenth embodiment, wherein the one or more feed or process streams comprise water.

A twenty-second embodiment, which is the chemical synthesis plant of the first or the third embodiment further comprising stored energy in the form of compressed hydrogen, compressed hydrocarbon(s) of the feed, compressed hydrocarbon products, cryogenic liquids, thermal batteries, electric batteries, phase change materials, or a combination thereof, such that the stored energy from the compressed hydrogen, the compressed hydrocarbon(s) from the feed, the compressed hydrocarbon products, the cryogenic liquids, the thermal batteries, the electric batteries, or the combination thereof can be utilized when renewable electricity is not available or economical.

A twenty-third embodiment, which is the chemical synthesis plant of the first or the third embodiment further comprising a blower, cooling water, and/or a refrigeration system to effect the at least a portion of the cooling.

A twenty-fourth embodiment, which is the chemical synthesis plant of the twenty-third embodiment, wherein the refrigeration system contains one or more electrically-driven compressors.

A twenty-fifth embodiment, which is the chemical synthesis plant of the first or the third embodiment, wherein a majority of a number of compressors utilized for the compressors are powered electrically.

A twenty-sixth embodiment, which is the chemical synthesis plant of the first or the third embodiment, configured such that a majority of the energy for pumping process and/or utility fluids is supplied electrically.

A twenty-seventh embodiment, which is the chemical synthesis plant of the first or the third embodiment, wherein the amount of hydrocarbon fuel consumed is decreased by at least 10% relative to that of an otherwise similar conventional chemical plant.

A twenty-eighth embodiment, which is the chemical synthesis plant of the first or the third embodiment, wherein the amount of $CO_2$ produced per ton of product is decreased by at least 10% relative to that of an otherwise similar conventional chemical plant.

A twenty-ninth embodiment, which is the chemical synthesis plant of the first or the third embodiment, wherein the specific energy consumption is decreased by at least 10% relative to that of an otherwise similar conventional chemical plant.

A thirtieth embodiment, which is the chemical synthesis plant of the first or the third embodiment, wherein the carbon efficiency is increased by at least 5% relative to that of an otherwise similar conventional chemical plant.

A thirty-first embodiment, which is a chemical synthesis plant wherein a majority (e.g., greater than 50, 60, 70, 80, 90, or 100%) of the net energy input conventionally provided by the combustion of a fuel is provided by electricity.

A thirty-second embodiment, which is a chemical synthesis plant wherein a majority of the net energy conventionally provided by the combustion of a fuel is provided by a non-carbon based energy source, a renewable energy source, and/or renewable electricity.

A thirty-third embodiment, which is the chemical synthesis plant of the thirty-first or the thirty-second embodiment, wherein (a) steam is not intentionally produced solely for the purpose of heat and/or energy transfer, (b) steam is not used as a primary or is not used at all as a heat and/or energy transfer medium, (c) steam is used only to facilitate the transfer of heat from one process stream to another, (d) steam is not utilized for mechanical work; or (e) all intentionally produced steam is generated electrically.

A thirty-fourth embodiment, which is the chemical synthesis plant of the thirty-first or the thirty-second embodiment, wherein the majority of the net energy is provided primarily by electricity from a renewable source.

A thirty-fifth embodiment, which is a chemical synthesis plant comprising one or more reactors configured for producing, from one or more reactants, a process stream comprising at least one chemical product, a feed preparation system configured to prepare one or more feed streams comprising one or more of the one or more reactants for introduction into the reactor; and/or a product purification system configured to separate the at least one chemical product from reaction byproducts, unreacted reactants, or a combination thereof within the process stream, wherein the chemical synthesis plant is configured (a) such that no combustion flue gas is produced, (b) without a substantially plant-wide steam system, (c) such that no steam is utilized therein to perform mechanical work, (d) such that any steam utilized as a diluent and/or reactant within the chemical synthesis plant is generated with electricity, (e) such that any steam utilized as a diluent and/or a reactant is superheated electrically to provide heat/raise the temperature of a process stream, (f) such that heat obtained from cooling process streams is utilized solely to preheat other process streams; or (g) any combination of (a)-(f).

Additional Disclosure Part III

The following are non-limiting, specific embodiments in accordance with the present disclosure:

Embodiments disclosed herein include:

A: A chemical synthesis plant for producing a desired chemical product, the chemical synthesis plant comprising: one or more streams that are heated or cooled prior to introduction into a subsequent unit; one or more streams that are compressed prior to introduction into a subsequent unit; one or more vessels that are maintained at a desired operating temperature or temperature profile therealong; or a combination thereof; wherein the chemical synthesis plant is configured such that a net energy input for the heating of the one or more streams that are heated, the cooling of the one or more streams that are cooled, the compressing of the one or more streams that are compressed, and the maintaining of the one or more vessels that are maintained at the desired operating temperature or temperature profile can be effected without combusting a carbon-based fuel externally to the one or more vessels.

B: A chemical synthesis plant for producing a desired chemical, the chemical synthesis plant comprising: one or more streams that are heated or cooled prior to introduction into a subsequent unit; one or more streams that are compressed prior to introduction into a subsequent unit; one or more vessels that are maintained at a desired operating temperature or temperature profile therealong; or a combination thereof; wherein the chemical synthesis plant is configured such that the net energy needed for a majority, substantially all, or greater than or equal to 10, 20, 30, 40, 50, 60, 70, 80, 90, or 100% of the heating of the one or more streams that are heated, the cooling of the one or more streams that are cooled, the compressing of the one or more streams that are compressed, and/or the maintaining of the one or more vessels that are maintained at the desired operating temperature or temperature profile can be effected with electricity from a renewable source, when available, and with electricity from a non-renewable source or via combustion of a fuel, when electricity from the renewable source is not available.

Each of embodiments A and B may have one or more of the following additional elements: Element 1: wherein the net energy needed for the heating, the cooling, the compressing, and the maintaining comprises, primarily comprises, consists, or consists essentially of a renewable energy. Element 2: wherein the energy comprises electricity. Element 3: wherein the electricity comprises electricity from a renewable source, electricity from a non-renewable source, or both. Element 4: wherein the renewable source comprises wind, solar, geothermal, hydroelectric, wave, tidal, nuclear or a combination thereof. Element 5: wherein a majority of the electricity is produced off-site. Element 6: wherein the one or more vessels comprises a reactor operable with a temperature profile along a length thereof, and wherein maintaining of the temperature profile via electricity enables enhanced control of the temperature profile relative to a reactor maintained at the operating temperature profile via combustion of a fuel. Element 7: wherein the chemical synthesis plant has a production capacity for the desired product of greater than or equal to about 100,000 tons per year. Element 8: wherein the heating, the cooling, the compressing, the maintaining, or a combination thereof is effected via a bifunctional apparatus operable via electricity and operable via combustion of a fuel, whereby the bifunctional apparatus can be operated via electricity from a renewable intermittent energy source, when available, and otherwise operated via electricity from a non-renewable source and/or the combustion of the fuel. Element 9: wherein the bifunctional apparatus comprises a compressor. Element 10: wherein steam is not intentionally produced unless it is utilized as a reactant or a diluent in a reactor. Element 11: wherein steam is utilized as a reactant, a diluent, or both, and wherein a majority, a portion, or substantially all of the steam is produced with electrical heating. Element 12: wherein a majority, a fraction, or substantially all apparatus utilized to provide the net energy for the heating, the cooling, the compressing, and/or the maintaining are electrically driven. Element 13: wherein the chemical synthesis plant is a steam cracking plant, an ammonia synthesis plant, or a methanol synthesis plant. Element 14: wherein the chemical synthesis plant is configured for the production of: propylene by cracking; ethylene oxide by oxidation of ethylene; monoethylene glycol by hydration of ethylene oxide; ethylene dichloride by chlorination of ethylene vinyl chloride from ethylene dichloride; alpha-olefins by oligomerization; olefins and/or diolefins by dehydrogenation of paraffins; isoparaffins by isomerization of normal paraffins; aromatics (BTX) from paraffins and/or naphthenes by cyclization and/or dehydrogenation; aromatics from naphtha by cyclization and/or dehydrogenation; ethylbenzene by alkylation of benzene with ethylene; styrene by dehydrogenation of ethyl benzene; cumene by alkylation of benzene with propylene; phenol by oxidation of cumene; terephthalic acid by the oxidation of paraxylene; oxygen by separation from air; nitrogen by separation from air; MTBE by etherification of isobutylene; and/or polyethylene, polypropylene, polyvinylchloride, polystyrene, polycarbonate, or polyethylene terephthalate (PE, PP, PVC, PS, PC, PET) by polymerization. Element 15: wherein the chemical synthesis plant is configured for the production of: acetic acid by methanol carbonylation; vinyl acetate by the reaction of acetic acid with ethylene; propylene by methanol oligomerization (generally known as the methanol-to-olefins process); aromatics by transalkylation or dealkylation; cyclohexane by hydrogenation of benzene; acrylic acid by oxidation of propylene; methacrolein by oxidation of isobutylene; methyl methacrylate by oxidation of methacrolein; acrylonitrile by ammoxidation of propylene; sulfuric acid by the oxidation of sulfur; nitric acid by the oxidation of ammonia; propylene glycol by the hydration of propylene; alcohols by hydroformylation of alkenes; esters, by condensation of carboxylic acids and alcohols; one or more nylon precursors selected from adipic acid, caprolactam, cyclohexanone, 1,6 diaminohexane, or a combination thereof; and/or polyvinyl alcohol (PVA), polyacrylates, polymethylmethacrylate (PMMA), nylons. Element 16: wherein, relative to a conventional and otherwise similar plant configured such that the net energy input for the heating of the one or more streams that are heated, the cooling of the one or more streams that are cooled, the compressing of the one or more streams that are compressed, and/or the maintaining of the one or more vessels that are maintained at the desired operating temperature or temperature profile are effected via combusting a fuel, the chemical synthesis plant produces a reduced level of emissions (e.g., of $CO_2$, nitrogen oxides, sulfur oxides, and/or volatile organic compounds). Element 17: wherein a conventional chemical synthesis plant for producing the chemical is configured for utilization of a portion of a component suitable as a feed component as a fuel to provide the net energy, and wherein, relative to the conventional chemical synthesis plant, the claimed chemical synthesis plant produces an additional amount of the desired chemical product from a given amount of the component suitable as the feed component. Element 18: wherein the chemical synthesis plant is configured such that a majority, a fraction, or substantially all of the energy input for the heating of the one or more streams that are heated, the cooling of the one or more streams that are cooled, the compressing of the one or more streams that are compressed, and/or the maintaining of the one or more vessels that are maintained at the desired operating temperature or temperature profile can be effected without utilizing steam as an intermediary energy carrier. Element 19: wherein the electricity from the renewable source comprises electricity produced via one or more off-site solar arrays, one or more off-site wind farms, one or more off-site hydroelectric generating stations, or a combination thereof. Element 20: further comprising hydrogen separation apparatus operable to separate hydrogen from one or more process streams (e.g., a purge stream), and apparatus operable to produce electricity, heat, and/or steam from at least a portion of the separated hydrogen. Element 21: further comprising storage apparatus configured for storing at least a portion of the separated hydrogen for later use to generate electricity, heat or steam. Element 22: wherein the apparatus operable to produce electricity, heat, and/or steam from at least a portion of the separated hydrogen comprises a fuel cell operable to produce electricity from the at least a portion of the separated hydrogen. Element 23: wherein the apparatus operable to produce electricity, heat, and/or steam from at least a portion of the separated hydrogen is configured to produce steam, and wherein the chemical synthesis plant is configured for utilization of the steam as a reactant and/or a diluent.

Additional Disclosure Part IV

The following are non-limiting, specific embodiments in accordance with the present disclosure:

A first embodiment, which is a chemical synthesis plant for producing a desired chemical product, the chemical synthesis plant comprising one or more streams that are heated or cooled prior to introduction into a subsequent unit, one or more streams that are compressed prior to introduction into a subsequent unit, one or more vessels that are maintained at a desired operating temperature or temperature profile therealong, or a combination thereof, wherein the chemical synthesis plant is configured such that a net energy input for the heating of the one or more streams that are heated, the cooling of the one or more streams that are cooled, the compressing of the one or more streams that are compressed, and the maintaining of the one or more vessels that are maintained at the desired operating temperature or temperature profile can be effected without combusting a carbon-based fuel externally to the one or more vessels.

A second embodiment, which is the chemical synthesis plant of the first embodiment, wherein the net energy needed for the heating, the cooling, the compressing, and the maintaining comprises, primarily comprises, consists, or consists essentially of a renewable energy.

A third embodiment, which is the chemical synthesis plant of the second embodiment, wherein the energy comprises electricity.

A fourth embodiment, which is the chemical synthesis plant of the third embodiment, wherein the electricity comprises electricity from a renewable source, electricity from a non-renewable source, or both.

A fifth embodiment, which is the chemical synthesis plant of the fourth embodiment, wherein the renewable source comprises wind, solar, geothermal, hydroelectric, wave, tidal, nuclear or a combination thereof.

A sixth embodiment, which is the chemical synthesis plant of the third embodiment, wherein a majority of the electricity is produced off-site.

A seventh embodiment, which is the chemical synthesis plant of the third embodiment, wherein the one or more vessels comprises a reactor operable with a temperature profile along a length thereof, and wherein maintaining of the temperature profile via electricity enables enhanced control of the temperature profile relative to a reactor maintained at the operating temperature profile via combustion of a fuel.

An eighth embodiment, which is the chemical synthesis plant of the first embodiment, wherein the chemical synthesis plant has a production capacity for the desired product of greater than or equal to about 100,000 tons per year.

A ninth embodiment, which is the chemical synthesis plant of the first embodiment, wherein the heating, the cooling, the compressing, the maintaining, or a combination thereof is effected via a bifunctional apparatus operable via electricity and operable via combustion of a fuel, whereby the bifunctional apparatus can be operated via electricity from a renewable intermittent energy source, when available, and otherwise operated via electricity from a non-renewable source and/or the combustion of the fuel.

A tenth embodiment, which is the chemical synthesis plant of the ninth embodiment, wherein the bifunctional apparatus comprises a compressor.

An eleventh embodiment, which is the chemical synthesis plant of the first embodiment, wherein steam is not intentionally produced unless it is utilized as a reactant or a diluent in a reactor.

A twelfth embodiment, which is the chemical synthesis plant of the first embodiment, wherein steam is utilized as a reactant, a diluent, or both, and wherein a majority, a portion, or substantially all of the steam is produced with electrical heating.

A thirteenth embodiment, which is the chemical synthesis plant of the first embodiment, wherein a majority, a fraction, or substantially all apparatus utilized to provide the net energy for the heating, the cooling, the compressing, and/or the maintaining are electrically driven.

A fourteenth embodiment, which is the chemical synthesis plant of the first embodiment, wherein the chemical synthesis plant is a steam cracking plant, an ammonia synthesis plant, or a methanol synthesis plant.

A fifteenth embodiment, which is the chemical synthesis plant of the first embodiment, wherein the chemical synthesis plant is configured for the production of propylene by cracking, ethylene oxide by oxidation of ethylene, monoethylene glycol by hydration of ethylene oxide, ethylene dichloride by chlorination of ethylene vinyl chloride from ethylene dichloride, alpha-olefins by oligomerization, olefins and/or diolefins by dehydrogenation of paraffins, isoparaffins by isomerization of normal paraffins, aromatics (BTX) from paraffins and/or naphthenes by cyclization and/or dehydrogenation, aromatics from naphtha by cyclization and/or dehydrogenation, ethylbenzene by alkylation of benzene with ethylene, styrene by dehydrogenation of ethyl benzene, cumene by alkylation of benzene with propylene, phenol by oxidation of cumene, terephthalic acid by the oxidation of paraxylene, oxygen by separation from air, nitrogen by separation from air, MTBE by etherification of isobutylene, and/or polyethylene, polypropylene, polyvinylchloride, polystyrene, polycarbonate, or polyethylene terephthalate (PE, PP, PVC, PS, PC, PET) by polymerization.

A sixteenth embodiment, which is the chemical synthesis plant of the first embodiment, wherein the chemical synthesis plant is configured for the production of acetic acid by methanol carbonylation, vinyl acetate by the reaction of acetic acid with ethylene, propylene by methanol oligomerization (generally known as the methanol-to-olefins process), aromatics by transalkylation or dealkylation, cyclohexane by hydrogenation of benzene, acrylic acid by oxidation of propylene, methacrolein by oxidation of isobutylene, methyl methacrylate by oxidation of methacrolein, acrylonitrile by ammoxidation of propylene, sulfuric acid by the oxidation of sulfur, nitric acid by the oxidation of ammonia, propylene glycol by the hydration of propylene, alcohols by hydroformylation of alkenes, esters, by condensation of carboxylic acids and alcohols, one or more nylon precursors selected from adipic acid, caprolactam, cyclohexanone, 1,6 diaminohexane, or a combination thereof, and/or polyvinyl alcohol (PVA), polyacrylates, polymethylmethacrylate (PMMA), nylons.

A seventeenth embodiment, which is the chemical synthesis plant of the first embodiment, wherein, relative to a conventional and otherwise similar plant configured such that the net energy input for the heating of the one or more streams that are heated, the cooling of the one or more streams that are cooled, the compressing of the one or more streams that are compressed, and/or the maintaining of the one or more vessels that are maintained at the desired operating temperature or temperature profile are effected via combusting a fuel, the chemical synthesis plant produces a reduced level of emissions (e.g., of $CO_2$, nitrogen oxides, sulfur oxides, and/or volatile organic compounds).

An eighteenth embodiment, which is the chemical synthesis plant of the first embodiment, wherein a conventional chemical synthesis plant for producing the chemical is configured for utilization of a portion of a component suitable as a feed component as a fuel to provide the net energy, and wherein, relative to the conventional chemical synthesis plant, the claimed chemical synthesis plant produces an additional amount of the desired chemical product from a given amount of the component suitable as the feed component.

A nineteenth embodiment, which is the chemical synthesis plant of the first embodiment, wherein the chemical synthesis plant is configured such that a majority, a fraction, or substantially all of the energy input for the heating of the one or more streams that are heated, the cooling of the one or more streams that are cooled, the compressing of the one or more streams that are compressed, and/or the maintaining of the one or more vessels that are maintained at the desired operating temperature or temperature profile can be effected without utilizing steam as an intermediary energy carrier.

A twentieth embodiment, which is a chemical synthesis plant for producing a desired chemical, the chemical synthesis plant comprising one or more streams that are heated or cooled prior to introduction into a subsequent unit, one or more streams that are compressed prior to introduction into a subsequent unit, one or more vessels that are maintained at a desired operating temperature or temperature profile therealong, or a combination thereof, wherein the chemical synthesis plant is configured such that the net energy needed for a majority, substantially all, or greater than or equal to 10, 20, 30, 40, 50, 60, 70, 80, 90, or 100% of the heating of the one or more streams that are heated, the cooling of the one or more streams that are cooled, the compressing of the one or more streams that are compressed, and/or the maintaining of the one or more vessels that are maintained at the desired operating temperature or temperature profile can be effected with electricity from a renewable source, when available, and with electricity from a non-renewable source or via combustion of a fuel, when electricity from the renewable source is not available.

A twenty-first embodiment, which is the chemical synthesis plant of the twentieth embodiment, wherein the electricity from the renewable source comprises electricity produced via one or more off-site solar arrays, one or more off-site wind farms, one or more off-site hydroelectric generating stations, or a combination thereof.

A twenty-second embodiment, which is the chemical synthesis plant of the twentieth embodiment further comprising hydrogen separation apparatus operable to separate hydrogen from one or more process streams (e.g., a purge stream), and apparatus operable to produce electricity, heat, and/or steam from at least a portion of the separated hydrogen.

A twenty-third embodiment, which is the chemical synthesis plant of the twenty-second embodiment further comprising storage apparatus configured for storing at least a portion of the separated hydrogen for later use to generate electricity, heat or steam.

A twenty-fourth embodiment, which is the chemical synthesis plant of the twenty-second embodiment, wherein the apparatus operable to produce electricity, heat, and/or steam from at least a portion of the separated hydrogen comprises a fuel cell operable to produce electricity from the at least a portion of the separated hydrogen.

A twenty-fifth embodiment, which is the chemical synthesis plant of the twenty-second embodiment, wherein the apparatus operable to produce electricity, heat, and/or steam from at least a portion of the separated hydrogen is configured to produce steam, and wherein the chemical synthesis plant is configured for utilization of the steam as a reactant and/or a diluent.

Additional Disclosure Part V

The following are non-limiting, specific embodiments in accordance with the present disclosure:

Embodiments disclosed herein include:

A: A chemical synthesis plant comprising: one or more reactors configured for producing, from one or more reactants, a process stream comprising at least one chemical product; a feed preparation system configured to prepare one or more feed streams comprising one or more of the one or more reactants for introduction into the one or more reactors; and/or a product purification system configured to separate the at least one chemical product from reaction byproducts, unreacted reactants, or a combination thereof within the process stream, (a) wherein at least one of the one or more reactors is configured such that a desired operating temperature or operating temperature profile therealong can be maintained without combusting a fuel or utilizing steam, produced by combusting a fuel, as an intermediate heat and/or energy transfer medium within the plant; (b) wherein the feed preparation system is configured to separate at least one component from the feed prior to introduction into the one or more reactors, to heat a feed stream to a desired reactor inlet temperature, to cool a feed stream to a desired reactor inlet temperature, to increase the pressure of a feed stream to a desired reactor inlet pressure, or a combination thereof, and is configured for operation without combusting fuel or utilizing steam, generated by combusting a fuel, as an intermediate heat and/or energy transfer medium within the plant; and/or (c) wherein the product purification system is configured to increase the pressure of the process stream, separate one or more components from the process stream via adjustment of the temperature and/or pressure thereof, or both, and is configured for operation without combusting a fuel or utilizing steam, generated by combusting a fuel, as an intermediate heat and/or energy transfer medium within the plant; or (d) a combination of (a)-(c).

B: A chemical synthesis plant for producing a primary chemical product, the chemical synthesis plant comprising: electrically powered, heated, or cooled apparatus utilized in place of 10, 20, 30, 40, 50, 60, 70, 80, 90, or 100% of steam-driven or combustion driven, heated, or cooled apparatus of a conventional chemical synthesis plant for producing the primary chemical product.

Each of embodiments A and B may have one or more of the following additional elements: Element 1: wherein the one or more reactors, the feed preparation system, the product purification system, or a combination thereof is configured for operation via renewable energy. Element 2: wherein the one or more reactors, the feed preparation system, the product purification system, or a combination thereof is configured for operation via electricity. Element 3: wherein the one or more reactors, the feed preparation system, the product purification system, or a combination thereof is bifunctionally configured for operation via electricity or combustion of a fuel. Element 4: wherein the feed preparation system, the product purification system, or both comprises a compressor that is bifunctionally configured for operation via electricity or combustion of a fuel. Element 5: wherein at least a portion, most, or all of the electricity is not produced on-site (i.e., comes from an external electricity grid). Element 6: wherein the electricity is produced via one or more off-site solar arrays, wind turbines, hydroelectric generating stations, tidal power stations, geothermal power stations, nuclear power stations, or a combination thereof. Element 7: wherein at least one of the one or more reactors is configured for operation with a desired temperature profile therealong, and wherein the desired operating profile is maintained via resistive heating or inductive heating. Element 8: wherein the resistive or inductive heating provides enhanced control of the desired temperature profile along the at least one reactor relative to maintaining of the desired temperature profile along a similar reactor via combustion of a fuel. Element 9: wherein the feed preparation system, the product purification system, or both comprise one or more distillation columns, and wherein some or all of the one or more distillation columns and/or associated reboilers are electrically heated. Element 10: wherein configuration of the one or more reactors, the feed preparation system, the product purification system, or a combination thereof for operation without combusting an external fuel provides for reduced emissions (e.g., carbon dioxide ($CO_2$) emissions) relative to a chemical synthesis plant that is substantially the same except for being configured for operation via the combusting of the fuel. Element 11: wherein a majority of the net energy input needed by the plant is provided by a non-carbon based energy source. Element 12: wherein configuration of the one or more reactors, the feed preparation system, and the product purification system for operation without combusting the fuel enables a light gas stream, a component selected from $C_1$ hydrocarbon (e.g., methane), $C_2$ hydrocarbons (e.g., ethane), $C_3$ hydrocarbons (e.g., propane), hydrogen, or a combination thereof to be recycled (e.g., as a feed component) within the chemical synthesis plant, sold, or utilized to produce another chemical in the or another chemical synthesis plant, thus providing economic benefit. Element 13: further comprising a recycle line configured to recycle the light gas stream, the component selected from $C_1$ hydrocarbon (e.g., methane), $C_2$ hydrocarbons (e.g., ethane), $C_3$ hydrocarbons (e.g., propane), hydrogen, or the combination thereof to at least one of the one or more reactors, wherein the light gas stream, the component selected from $C_1$ hydrocarbon (e.g., methane), $C_2$ hydrocarbons (e.g., ethane), $C_3$ hydrocarbons, hydrogen, or the combination thereof is conventionally flared or burned as a fuel. Element 14: wherein the chemical synthesis plant is a steam cracking plant, an ammonia synthesis plant, or a methanol synthesis plant. Element 15: wherein the chemical synthesis plant is configured for the production of: propylene by cracking; ethylene oxide by oxidation of ethylene; monoethylene glycol by hydration of ethylene oxide; ethylene dichloride by chlorination of ethylene; vinyl chloride from ethylene dichloride; alpha-olefins by oligomerization; olefins and/or diolefins by dehydrogenation of paraffins; isoparaffins by isomerization of normal paraffins; aromatics (BTX) from paraffins and/or naphthenes by cyclization and/or dehydrogenation; aromatics from naphtha by cyclization and/or dehydrogenation; ethylbenzene by alkylation of benzene with ethylene; styrene by dehydrogenation of ethyl benzene; cumene by alkylation of benzene with propylene; phenol by oxidation of cumene; terephthalic acid by the oxidation of paraxylene; oxygen by separation from air; nitrogen by separation from air; MTBE by etherification of isobutylene; and/or polyethylene, polypropylene, polyvinylchloride, polystyrene, polycarbonate, or polyethylene terephthalate (PE, PP, PVC, PS, PC, PET) by polymerization. Element 16: wherein the chemical synthesis plant is configured for the production of: acetic acid by methanol carbonylation; vinyl acetate by the reaction of acetic acid with ethylene; propylene by methanol oligomerization (generally known as the methanol-to-olefins process); aromatics by transalkylation or dealkylation; cyclohexane by hydrogenation of benzene; acrylic acid by oxidation of propylene; methacrolein by oxidation of isobutylene; methyl methacrylate by oxidation of methacrolein; acrylonitrile by ammoxidation of propylene; sulfuric acid by the oxidation of sulfur; nitric acid by the oxidation of ammonia; propylene glycol by the hydration of propylene; alcohols by hydroformylation of alkenes; esters, by condensation of carboxylic acids and alcohols; one or more nylon precursors selected from adipic acid, caprolactam, cyclohexanone, 1,6 diaminohexane, or a combination thereof; and/or polyvinyl alcohol (PVA), polyacrylates, polymethylmethacrylate (PMMA), nylons. Element 17: wherein configuration of the feed preparation system, the one or more reactors, and/or the product purification system without combusting a fuel or utilizing steam as a heat transfer medium increases the energy efficiency of the chemical synthesis plant and/or reduces the carbon emissions relative to a conventional chemical synthesis plant wherein the feed preparation system, the one or more reactors, and/or the product purification system is configured for combusting a fuel and/or utilizing steam as a heat transfer medium. Element 18: wherein the energy efficiency provided by the chemical synthesis plant can be increased by at least 5, 10, 20, 30, 40, 50, 60, or 70% relative to the conventional chemical production system. Element 19: comprising: electrically-driven compressors and no compressors driven by gas, steam, or steam produced via combustion; and/or no apparatus configured for the production and/or utilization of steam or steam generated by combustion of a fuel solely or primarily as an intermediate heat and/or energy transfer apparatus. Element 20: comprising electrically-driven, heated, or cooled apparatus in place of a majority of the steam-driven or combustion driven, heated, or cooled apparatus of the conventional chemical synthesis plant for producing the primary chemical product.

Additional Disclosure Part VI

The following are non-limiting, specific embodiments in accordance with the present disclosure:

A first embodiment, which is a chemical synthesis plant comprising one or more reactors configured for producing, from one or more reactants, a process stream comprising at least one chemical product, a feed preparation system configured to prepare one or more feed streams comprising one or more of the one or more reactants for introduction into the one or more reactors, and/or a product purification system configured to separate the at least one chemical product from reaction byproducts, unreacted reactants, or a combination thereof within the process stream, (a) wherein at least one of the one or more reactors is configured such that a desired operating temperature or operating temperature profile therealong can be maintained without combusting a fuel or utilizing steam, produced by combusting a fuel, as an intermediate heat and/or energy transfer medium within the plant, (b) wherein the feed preparation system is configured to separate at least one component from the feed prior to introduction into the one or more reactors, to heat a feed stream to a desired reactor inlet temperature, to cool a feed stream to a desired reactor inlet temperature, to increase the pressure of a feed stream to a desired reactor inlet pressure, or a combination thereof, and is configured for operation without combusting fuel or utilizing steam, generated by combusting a fuel, as an intermediate heat and/or energy transfer medium within the plant, and/or (c) wherein the product purification system is configured to increase the pressure of the process stream, separate one or more components from the process stream via adjustment of the temperature and/or pressure thereof, or both, and is configured for operation without combusting a fuel or utilizing steam, generated by combusting a fuel, as an intermediate heat and/or energy transfer medium within the plant, or (d) a combination of (a)-(c).

A second embodiment, which is the chemical synthesis plant of the first embodiment, wherein the one or more reactors, the feed preparation system, the product purification system, or a combination thereof is configured for operation via renewable energy.

A third embodiment, which is the chemical synthesis plant of the first or the second embodiment, wherein the one or more reactors, the feed preparation system, the product purification system, or a combination thereof is configured for operation via electricity.

A fourth embodiment, which is the chemical synthesis plant of the third embodiment, wherein the one or more reactors, the feed preparation system, the product purification system, or a combination thereof is bifunctionally configured for operation via electricity or combustion of a fuel.

A fifth embodiment, which is the chemical synthesis plant of the fourth embodiment, wherein the feed preparation system, the product purification system, or both comprises a compressor that is bifunctionally configured for operation via electricity or combustion of a fuel.

A sixth embodiment, which is the chemical synthesis plant of the third embodiment, wherein at least a portion, most, or all of the electricity is not produced on-site (i.e., comes from an external electricity grid).

A seventh embodiment, which is the chemical synthesis plant of the sixth embodiment, wherein the electricity is produced via one or more off-site solar arrays, wind turbines, hydroelectric generating stations, tidal power stations, geothermal power stations, nuclear power stations, or a combination thereof.

An eighth embodiment, which is the chemical synthesis plant of the first embodiment, wherein at least one of the one or more reactors is configured for operation with a desired temperature profile therealong, and wherein the desired operating profile is maintained via resistive heating or inductive heating.

A ninth embodiment, which is the chemical synthesis plant of the eighth embodiment, wherein the resistive or inductive heating provides enhanced control of the desired temperature profile along the at least one reactor relative to maintaining of the desired temperature profile along a similar reactor via combustion of a fuel.

A tenth embodiment, which is the chemical synthesis plant of the first embodiment, wherein the feed preparation system, the product purification system, or both comprise one or more distillation columns, and wherein some or all of the one or more distillation columns and/or associated reboilers are electrically heated.

An eleventh embodiment, which is the chemical synthesis plant of the first embodiment, wherein configuration of the one or more reactors, the feed preparation system, the product purification system, or a combination thereof for operation without combusting an external fuel provides for reduced emissions (e.g., carbon dioxide ($CO_2$) emissions) relative to a chemical synthesis plant that is substantially the same except for being configured for operation via the combusting of the fuel.

A twelfth embodiment, which is the chemical synthesis plant of the first embodiment, wherein a majority of the net energy input needed by the plant is provided by a non-carbon based energy source.

A thirteenth embodiment, which is the chemical synthesis plant of the first embodiment, wherein configuration of the one or more reactors, the feed preparation system, and the product purification system for operation without combusting the fuel enables a light gas stream, a component selected from $C_1$ hydrocarbon (e.g., methane), $C_2$ hydrocarbons (e.g., ethane), $C_3$ hydrocarbons (e.g., propane), hydrogen, or a combination thereof to be recycled (e.g., as a feed component) within the chemical synthesis plant, sold, or utilized to produce another chemical in the or another chemical synthesis plant, thus providing economic benefit.

A fourteenth embodiment, which is the chemical synthesis plant of the thirteenth embodiment further comprising a recycle line configured to recycle the light gas stream, the component selected from $C_1$ hydrocarbon (e.g., methane), $C_2$ hydrocarbons (e.g., ethane), $C_3$ hydrocarbons (e.g., propane), hydrogen, or the combination thereof to at least one of the one or more reactors, wherein the light gas stream, the component selected from $C_1$ hydrocarbon (e.g., methane), $C_2$ hydrocarbons (e.g., ethane), $C_3$ hydrocarbons, hydrogen, or the combination thereof is conventionally flared or burned as a fuel.

A fifteenth embodiment, which is the chemical synthesis plant of the first embodiment, wherein the chemical synthesis plant is a steam cracking plant, an ammonia synthesis plant, or a methanol synthesis plant.

A sixteenth embodiment, which is the chemical synthesis plant of the first embodiment, wherein the chemical synthesis plant is configured for the production of propylene by cracking, ethylene oxide by oxidation of ethylene, monoethylene glycol by hydration of ethylene oxide, ethylene dichloride by chlorination of ethylene, vinyl chloride from ethylene dichloride, alpha-olefins by oligomerization, olefins and/or diolefins by dehydrogenation of paraffins, isoparaffins by isomerization of normal paraffins, aromatics (BTX) from paraffins and/or naphthenes by cyclization and/or dehydrogenation, aromatics from naphtha by cyclization and/or dehydrogenation, ethylbenzene by alkylation of benzene with ethylene, styrene by dehydrogenation of ethyl benzene, cumene by alkylation of benzene with propylene, phenol by oxidation of cumene, terephthalic acid by the oxidation of paraxylene, oxygen by separation from air, nitrogen by separation from air, MTBE by etherification of isobutylene, and/or polyethylene, polypropylene, polyvinylchloride, polystyrene, polycarbonate, or polyethylene terephthalate (PE, PP, PVC, PS, PC, PET) by polymerization.

A seventeenth embodiment, which is the chemical synthesis plant of the first embodiment, wherein the chemical synthesis plant is configured for the production of: acetic acid by methanol carbonylation, vinyl acetate by the reaction of acetic acid with ethylene, propylene by methanol oligomerization (generally known as the methanol-to-olefins process), aromatics by transalkylation or dealkylation, cyclohexane by hydrogenation of benzene, acrylic acid by oxidation of propylene, methacrolein by oxidation of isobutylene, methyl methacrylate by oxidation of methacrolein, acrylonitrile by ammoxidation of propylene, sulfuric acid by the oxidation of sulfur, nitric acid by the oxidation of ammonia, propylene glycol by the hydration of propylene, alcohols by hydroformylation of alkenes, esters, by condensation of carboxylic acids and alcohols, one or more nylon precursors selected from adipic acid, caprolactam, cyclohexanone, 1,6 diaminohexane, or a combination thereof, and/or polyvinyl alcohol (PVA), polyacrylates, polymethylmethacrylate (PMMA), nylons.

An eighteenth embodiment, which is the chemical synthesis plant of the first embodiment, wherein configuration of the feed preparation system, the one or more reactors, and/or the product purification system without combusting a fuel or utilizing steam as a heat transfer medium increases the energy efficiency of the chemical synthesis plant and/or reduces the carbon emissions relative to a conventional chemical synthesis plant wherein the feed preparation system, the one or more reactors, and/or the product purification system is configured for combusting a fuel and/or utilizing steam as a heat transfer medium.

A nineteenth embodiment, which is the chemical production system of the eighteenth embodiment, wherein the energy efficiency provided by the chemical synthesis plant can be increased by at least 5, 10, 20, 30, 40, 50, 60, or 70% relative to the conventional chemical production system.

A twentieth embodiment, which is a chemical synthesis plant for producing a primary chemical product, the chemical synthesis plant comprising electrically powered, heated, or cooled apparatus utilized in place of 10, 20, 30, 40, 50, 60, 70, 80, 90, or 100% of steam-driven or combustion driven, heated, or cooled apparatus of a conventional chemical synthesis plant for producing the primary chemical product.

A twenty-first embodiment, which is the chemical synthesis plant of the twentieth embodiment comprising electrically-driven compressors and no compressors driven by gas, steam, or steam produced via combustion, and/or no apparatus configured for the production and/or utilization of steam or steam generated by combustion of a fuel solely or primarily as an intermediate heat and/or energy transfer apparatus.

A twenty-second embodiment, which is the chemical synthesis plant of the twentieth embodiment comprising electrically-driven, heated, or cooled apparatus in place of a majority of the steam-driven or combustion driven, heated, or cooled apparatus of the conventional chemical synthesis plant for producing the primary chemical product.

A twenty-third embodiment, which is a chemical synthesis plant as described herein.

Additional Disclosure Part VII

The following are non-limiting, specific embodiments in accordance with the present disclosure:
Embodiments Disclosed Herein Include:

A: A method of producing a chemical product, the method comprising: preparing one or more feed streams comprising one or more reactants for introduction into a reactor; reacting the one or more reactants in the reactor to produce a product stream comprising the chemical product; separating the chemical product from reaction byproducts, unreacted reactants, or a combination thereof within the product stream; and/or optionally recycling one or more of the unreacted reactants and/or reaction byproducts, wherein a majority, greater than 20, 30, 40, 50, 60, 70, 80, or 90%, or substantially all of the net energy needed for powering, pumping, heating, cooling, compressing, separating, or a combination thereof utilized for one or more of the preparing, the reacting, the separating, the recycling, or a combination thereof is provided from a non-carbon based energy source, from a renewable energy source, and/or from electricity.

B: A method of increasing energy efficiency during operation of a chemical plant, the method comprising: replacing heating conventionally provided by burning a carbon-based fuel by heating provided by electricity; minimizing or eliminating the use of an elaborate steam system for transfer of heat and/or energy throughout the chemical plant; and powering units conventionally powered via combustion of a fuel or by a product produced via combustion of a fuel (e.g., steam produced via combustion of a fuel) with electricity.

C: A method of operating a chemical synthesis plant, the method comprising: providing a majority, greater than 20, 30, 40, 50, 60, 70, 80, or 90%, or substantially all of the net energy (e.g., in first category C1) conventionally supplied directly as thermal energy by the combustion of fuel, the net energy (e.g., in second category C2) utilized for heating of various chemical streams, and/or the energy (e.g., in third category C3) utilized to perform mechanical work without combusting a carbon-based energy source, with renewable energy, such as renewable electricity, and/or with electricity (e.g.., with electricity from any source, renewable and/or non-renewable).

Each of embodiments A, B, and C may have one or more of the following additional elements: Element 1: further comprising not utilizing steam primarily as a heat and/or energy transfer medium throughout the chemical production. Element 2: further comprising not producing steam with heat provided by combustion of a fuel. Element 3: comprising providing substantially all of the net energy needed for compressing from electricity. Element 4: wherein providing substantially all of the net energy needed for compressing from electricity comprises compressing via an electric motor-driven compressor or a turbine-driven compressor driven by electrically produced steam. Element 5: comprising providing a majority, greater than 20, 30, 40, 50, 60, 70, 80, or 90%, or substantially all of the net energy utilized by the method from electricity. Element 6: further comprising providing at least 25 MW of electricity. Element 7: further comprising utilizing for a majority, most, or at least 20, 30, 40, 50, 60, 70, 80 or 90% of the electricity, electricity from a renewable source. Element 8: wherein the renewable source comprises hydroelectric, solar, wind, geothermal, nuclear, wave, tide, or a combination thereof. Element 9: wherein the chemical product comprises olefins, ammonia, or methanol. Element 10: wherein providing a majority of the net energy needed for powering, pumping, heating, cooling, compressing, separating, or a combination thereof utilized for one or more of the preparing, the reacting, the separating, the recycling, or the combination thereof from a non-carbon based energy source, from a renewable energy source, and/or from electricity further comprises regenerating one or more guard beds, adsorbers, absorbers, process gas dryers, strippers, and/or some catalysts via electrical heating, the addition of electrically-compressed gases, and/or the addition of electrically-generated steam. Element 11: wherein replacing heating conventionally provided by burning a carbon-based fuel by electrical heating comprises replacing a reactor heated by the combustion of a fuel by an electrically heated reactor. Element 12: wherein the electrically heated reactor provides control of a temperature profile along the length thereof such that conversion and/or selectivity are increased and/or rates of deactivation and/or fouling are decreased relative to a reactor in which the temperature profile is not electrically controlled. Element 13: wherein powering units conventionally powered via combustion of a fuel or a product produced via combustion of a fuel comprises utilizing electric motor-driven compressors or turbine-driven compressors driven by electrically produced steam to provide compression rather than gas fired turbines or turbines driven by steam produced via combustion of a fuel. Element 14: wherein minimizing or eliminating the use of an elaborate steam system for transfer of heat and/or energy throughout the chemical plant comprises replacing steam heated reboilers and/or distillation columns with electrically heated reboilers and/or distillation columns. Element 15: wherein replacing heating conventionally provided by burning a carbon-based fuel by electrical heating comprises replacing reboilers and/or distillation columns heated either directly or indirectly via combustion with electrically heated reboilers and/or distillation columns. Element 16: further comprising utilizing for a majority, most, or at least 20, 30, 40, 50, 60, 70, 80 or 90% of the electricity, electricity from a renewable source. Element 17: wherein the electricity comprises renewable electricity from an IES, and wherein at least 20, 30, 40, or 50% of a plant online time, the electricity is provided from the IES. Element 18: wherein replacing heating conventionally provided by burning a carbon-based fuel by heating provided by electricity and/or powering units conventionally powered via combustion of a fuel or by a product produced via combustion of a fuel with electricity results in a reduction in greenhouse gas (GHG) emissions by the chemical plant. Element 19: wherein the chemical plant comprises a steam cracking plant, an ammonia synthesis plant, or a methanol synthesis plant. Element 20: wherein replacing heating conventionally provided by burning a carbon-based fuel by heating provided by electricity comprises heating of one or more gas streams via resistive or inductive heating. Element 21: wherein replacing heating conventionally provided by burning a carbon-based fuel by heating provided by electricity comprises heating of one or more reactors via resistive or inductive heating. Element 22: wherein replacing heating conventionally provided by burning a carbon-based fuel by heating provided by electricity comprises heating of one or more reactors via a radiant section in which heat generated electrically is used to heat radiative panels which transfer heat to the one or more reactors by radiation. Element 23: wherein the powering with electricity is accomplished by means of a vapor compression heat pumping system.

Additional Disclosure Part VIII

The following are non-limiting, specific embodiments in accordance with the present disclosure:

A first embodiment, which is a method of producing a chemical product, the method comprising preparing one or more feed streams comprising one or more reactants for introduction into a reactor, reacting the one or more reactants in the reactor to produce a product stream comprising the chemical product, separating the chemical product from reaction byproducts, unreacted reactants, or a combination thereof within the product stream, and/or recycling one or more of the unreacted reactants and/or reaction byproducts, wherein a majority, greater than 20, 30, 40, 50, 60, 70, 80, or 90%, or substantially all of the net energy needed for powering, pumping, heating, cooling, compressing, separating, or a combination thereof utilized for one or more of the preparing, the reacting, the separating, the recycling, or a combination thereof is provided from a non-carbon based energy source, from a renewable energy source, and/or from electricity.

A second embodiment, which is the method of the first embodiment further comprising not utilizing steam primarily as a heat and/or energy transfer medium throughout the chemical production.

A third embodiment, which is the method of the first embodiment further comprising not producing steam with heat provided by combustion of a fuel.

A fourth embodiment, which is the method of the first embodiment comprising providing substantially all of the net energy needed for compressing from electricity.

A fifth embodiment, which is the method of the fourth embodiment, wherein providing substantially all of the net energy needed for compressing from electricity comprises compressing via an electric motor-driven compressor or a turbine-driven compressor driven by electrically produced steam.

A sixth embodiment, which is the method of the first embodiment, comprising providing a majority, greater than 20, 30, 40, 50, 60, 70, 80, or 90%, or substantially all of the net energy utilized by the method from electricity.

A seventh embodiment, which is the method of the first embodiment further comprising providing at least 25 MW of electricity.

An eighth embodiment, which is the method of the first embodiment further comprising utilizing for a majority, most, or at least 20, 30, 40, 50, 60, 70, 80 or 90% of the electricity, electricity from a renewable source.

A ninth embodiment, which is the method of the eighth embodiment, wherein the renewable source comprises hydroelectric, solar, wind, geothermal, nuclear, wave, tide, or a combination thereof.

A tenth embodiment, which is the method of the first embodiment, wherein the chemical product comprises olefins, ammonia, or methanol.

An eleventh embodiment, which is the method of the first embodiment, wherein providing a majority of the net energy needed for powering, pumping, heating, cooling, compressing, separating, or a combination thereof utilized for one or more of the preparing, the reacting, the separating, the recycling, or the combination thereof from a non-carbon based energy source, from a renewable energy source, and/or from electricity further comprises regenerating one or more guard beds, adsorbers, absorbers, process gas dryers, strippers, and/or some catalysts via electrical heating, the addition of electrically-compressed gases, and/or the addition of electrically-generated steam.

A twelfth embodiment, which is a method of increasing energy efficiency during operation of a chemical plant, the method comprising replacing heating conventionally provided by burning a carbon-based fuel by heating provided by electricity, minimizing or eliminating the use of an elaborate steam system for transfer of heat, and/or energy throughout the chemical plant, and powering units conventionally powered via combustion of a fuel or by a product produced via combustion of a fuel (e.g., steam produced via combustion of a fuel) with electricity.

A thirteenth embodiment, which is the method of the twelfth embodiment, wherein replacing heating conventionally provided by burning a carbon-based fuel by electrical heating comprises replacing a reactor heated by the combustion of a fuel by an electrically heated reactor.

A fourteenth embodiment, which is the method of the thirteenth embodiment, wherein the electrically heated reactor provides control of a temperature profile along the length thereof such that conversion and/or selectivity are increased and/or rates of deactivation and/or fouling are decreased relative to a reactor in which the temperature profile is not electrically controlled.

A fifteenth embodiment, which is the method of the twelfth embodiment, wherein powering units conventionally powered via combustion of a fuel or a product produced via combustion of a fuel comprises utilizing electric motor-driven compressors or turbine-driven compressors driven by electrically produced steam to provide compression rather than gas fired turbines or turbines driven by steam produced via combustion of a fuel.

A sixteenth embodiment, which is the method of the twelfth embodiment, wherein minimizing or eliminating the use of an elaborate steam system for transfer of heat and/or energy throughout the chemical plant comprises replacing steam heated reboilers and/or distillation columns with electrically heated reboilers and/or distillation columns.

A seventeenth embodiment, which is the method of the twelfth embodiment, wherein replacing heating conventionally provided by burning a carbon-based fuel by electrical heating comprises replacing reboilers and/or distillation columns heated either directly or indirectly via combustion with electrically heated reboilers and/or distillation columns.

An eighteenth embodiment, which is the method of the twelfth embodiment further comprising utilizing for a majority, most, or at least 20, 30, 40, 50, 60, 70, 80 or 90% of the electricity, electricity from a renewable source.

A nineteenth embodiment, which is the method of the eighteenth embodiment, wherein the electricity comprises renewable electricity from an IES, and wherein at least 20, 30, 40, or 50% of a plant online time, the electricity is provided from the IES.

A twentieth embodiment, which is the method of the twelfth embodiment, wherein replacing heating conventionally provided by burning a carbon-based fuel by heating provided by electricity and/or powering units conventionally powered via combustion of a fuel or by a product produced via combustion of a fuel with electricity results in a reduction in greenhouse gas (GHG) emissions by the chemical plant.

A twenty-first embodiment, which is the method of the twelfth embodiment, wherein the chemical plant comprises a steam cracking plant, an ammonia synthesis plant, or a methanol synthesis plant.

A twenty-second embodiment, which is the method of the twelfth embodiment, wherein replacing heating conventionally provided by burning a carbon-based fuel by heating provided by electricity comprises heating of one or more gas streams via resistive or inductive heating.

A twenty-third embodiment, which is the method of the twelfth embodiment, wherein replacing heating conventionally provided by burning a carbon-based fuel by heating provided by electricity comprises heating of one or more reactors via resistive or inductive heating.

A twenty-fourth embodiment, which is the method of the twelfth embodiment, wherein replacing heating conventionally provided by burning a carbon-based fuel by heating provided by electricity comprises heating of one or more reactors via a radiant section in which heat generated electrically is used to heat radiative panels which transfer heat to the one or more reactors by radiation.

A twenty-fifth embodiment, which is the method of the twelfth embodiment, wherein the powering with electricity is accomplished by means of a vapor compression heat pumping system.

A twenty-sixth embodiment, which is a method of operating a chemical synthesis plant, the method comprising providing a majority, greater than 20, 30, 40, 50, 60, 70, 80, or 90%, or substantially all of the net energy (e.g., in first category C1) conventionally supplied directly as thermal energy by the combustion of fuel, the net energy (e.g., in second category C2) utilized for heating of various chemical streams, and/or the energy (e.g., in third category C3) utilized to perform mechanical work without combusting a carbon-based energy source, with renewable energy, such as renewable electricity, and/or with electricity (e.g.., with electricity from any source, renewable and/or non-renewable).

Additional Disclosure Part IX

The following are non-limiting, specific embodiments in accordance with the present disclosure:

Embodiments Disclosed Herein Include:

A: A method of increasing energy efficiency during operation of a chemical synthesis plant for synthesis of at least one chemical product, the method comprising: eliminating more than 10, 20, 30, 40, 50, 60, 70, 80, 90, or substantially all of the steam produced by a steam system configured to transfer heat and/or energy throughout the plant.

B: A method of operating, designing, and/or retrofitting a chemical synthesis plant, the method comprising: replacing heating provided in a conventional plant by burning a carbon-based fuel by heating provided by electricity.

C: A method of operating a chemical plant, the method comprising: replacing an amount of energy conventionally produced via burning of carbon-based fuel(s) by electricity, such that the greenhouse gas emissions produced by the chemical plant are reduced by greater than or equal to about 5, 10, 20, 30, 40, 50, 60, 70, 80, 90, or 100% relative to a conventional chemical plant operated with the amount of energy produced via burning of the carbon-based fuel(s).

Each of embodiments A, B, and C may have one or more of the following additional elements: Element 1: wherein eliminating more than 10, 20, 30, 40, 50, 60, 70, 80, 90, or substantially all of the steam produced by the steam system configured to transfer heat and/or energy throughout the chemical synthesis plant comprises replacing steam turbines with electric motors, replacing steam heated reboilers with electrically heated reboilers, or both. Element 2: further comprising electrically providing a majority, at least 10, 20, 30, 40, 50, 60, 70, 80, 90, or substantially all of the heat conventionally provided throughout the chemical synthesis plant by heat transfer with the steam. Element 3: wherein the chemical synthesis plant is a steam cracking plant, an ammonia synthesis plant, or a methanol synthesis plant. Element 4: wherein replacing heating provided in a conventional plant by burning a carbon-based fuel by heating provided by electricity reduces greenhouse gas emissions from the chemical synthesis plant by at least about 10, 20, 25, 30, 35, 40, 45, 50, 55, 60, 65, 70, 75, 80, 85, 90, 95 or substantially 100% relative to a conventional chemical synthesis plant operated with heating provided by burning the carbon-based fuel. Element 5: wherein the conventional plant is operated with heating provided by burning a portion of a feed component as a carbon-based fuel, and wherein replacing heating provided in a conventional plant by burning the carbon-based fuel by heating provided by electricity increases the amount of a chemical product produced from a supply of the feed component relative to an amount of the chemical product produced from a supply of the feed component in the conventional plant. Element 6: wherein replacing heating provided in a conventional plant either directly or indirectly by burning a carbon-based fuel by heating provided by electricity comprises replacing one or more reactors conventionally maintained at an operating temperature by burning a fuel by one or more electrically heated reactors. Element 7: wherein the one or more reactors are selected from steam reformers, pre-reformers, pyrolysis furnaces, dehydrogenation reactors, catalytic naphtha reformers, dealkylation reactors, fixed-bed reactors, fluidized bed reactors, stirred tank reactors, and combinations thereof. Element 8: wherein replacing heating provided in a conventional plant by burning a carbon-based fuel by heating provided by electricity comprises replacing one or more, most, or all heat exchangers of the chemical synthesis plant with one or more electric heaters. Element 9: wherein replacing heating provided in a conventional plant by burning a carbon-based fuel by heating provided by electricity comprises replacing one or more, most, or all feed preheaters of the chemical synthesis plant with one or more electric heaters. Element 10: wherein replacing heating provided in a conventional plant by burning a carbon-based fuel by heating provided by electricity comprises replacing one or more, most, or all reboilers of the chemical plant heated by steam or gas combustion with an electrically heated reboiler. Element 11: wherein replacing heating provided in a conventional plant by burning a carbon-based fuel by heating provided by electricity comprises replacing one or more, most, or all distillation columns with an electrically heated distillation column. Element 12: wherein a majority, at least 10, 20, 30, 40, 50, 60, 70, 80, 90, or substantially all of the electricity is renewable electricity from a renewable energy source. Element 13: further comprising not utilizing steam as a primary heat and/or energy transfer medium to transfer heat throughout the chemical synthesis plant. Element 14: wherein not utilizing steam as a primary heat and/or energy transfer medium to transfer heat and/or energy throughout the chemical synthesis plant comprises replacing a majority, at least 10, 20, 30, 40, 50, 60, 70, 80, 90, or substantially all of the steam-turbine drives of the chemical synthesis plant with electric motors. Element 15: wherein not utilizing steam as a primary heat and/or transfer medium to transfer heat throughout the chemical synthesis plant comprises replacing a majority, at least 10, 20, 30, 40, 50, 60, 70, 80, 90, or substantially all of the steam-heated reboilers of the chemical synthesis plant with electrically-heated reboilers. Element 16: wherein the chemical synthesis plant is a steam cracking plant, an ammonia synthesis plant, or a methanol synthesis plant. Element 17: further comprising utilizing electrical heating of low temperature steam to further increase the energy efficiency. Element 18: wherein the at least one chemical product comprises: propylene; ethylene oxide; monoethylene glycol; ethylene dichloride; vinyl chloride; one or more olefins; one or more diolefins; one or more isoparaffins; one or more aromatics; cyclohexane; ethylbenzene; styrene; cumene; phenol; terephthalic acid; oxygen; nitrogen; methyl tert-butyl ether (MTBE); polyethylene; polypropylene; polyvinylchloride; polystyrene; polycarbonate; polyethylene terephthalate; or a combination thereof. Element 19: wherein the chemical plant is a steam cracking plant, an ammonia synthesis plant, or a methanol synthesis plant.

Additional Disclosure Part X

The following are non-limiting, specific embodiments in accordance with the present disclosure:

A first embodiment, which is a method of increasing energy efficiency during operation of a chemical synthesis plant for synthesis of at least one chemical product, the method comprising eliminating more than 10, 20, 30, 40, 50, 60, 70, 80, 90, or substantially all of the steam produced by a steam system configured to transfer heat and/or energy throughout the plant.

A second embodiment, which is the method of the first embodiment, wherein eliminating more than 10, 20, 30, 40, 50, 60, 70, 80, 90, or substantially all of the steam produced by the steam system configured to transfer heat and/or energy throughout the chemical synthesis plant comprises replacing steam turbines with electric motors, replacing steam heated reboilers with electrically heated reboilers, or both.

A third embodiment, which is the method of the first embodiment further comprising electrically providing a majority, at least 10, 20, 30, 40, 50, 60, 70, 80, 90, or substantially all of the heat conventionally provided throughout the chemical synthesis plant by heat transfer with the steam.

A fourth embodiment, which is the method of the first embodiment, wherein the chemical synthesis plant is a steam cracking plant, an ammonia synthesis plant, or a methanol synthesis plant.

A fifth embodiment, which is a method of operating, designing, and/or retrofitting a chemical synthesis plant, the method comprising replacing heating provided in a conventional plant by burning a carbon-based fuel by heating provided by electricity.

A sixth embodiment, which is the method of the fifth embodiment, wherein replacing heating provided in a conventional plant by burning a carbon-based fuel by heating provided by electricity reduces greenhouse gas emissions from the chemical synthesis plant by at least about 10, 20, 25, 30, 35, 40, 45, 50, 55, 60, 65, 70, 75, 80, 85, 90, 95 or substantially 100% relative to a conventional chemical synthesis plant operated with heating provided by burning the carbon-based fuel.

A seventh embodiment, which is the method of the fifth embodiment, wherein the conventional plant is operated with heating provided by burning a portion of a feed component as a carbon-based fuel, and wherein replacing heating provided in a conventional plant by burning the carbon-based fuel by heating provided by electricity increases the amount of a chemical product produced from a supply of the feed component relative to an amount of the chemical product produced from a supply of the feed component in the conventional plant.

An eighth embodiment, which is the method of the fifth embodiment, wherein replacing heating provided in a conventional plant either directly or indirectly by burning a carbon-based fuel by heating provided by electricity comprises replacing one or more reactors conventionally maintained at an operating temperature by burning a fuel by one or more electrically heated reactors.

A ninth embodiment, which is the method of the eighth embodiment, wherein the one or more reactors are selected from steam reformers, pre-reformers, pyrolysis furnaces, dehydrogenation reactors, catalytic naphtha reformers, dealkylation reactors, fixed-bed reactors, fluidized bed reactors, stirred tank reactors, and combinations thereof.

A tenth embodiment, which is the method of the fifth embodiment, wherein replacing heating provided in a conventional plant by burning a carbon-based fuel by heating provided by electricity comprises replacing one or more, most, or all heat exchangers of the chemical synthesis plant with one or more electric heaters.

An eleventh embodiment, which is the method of the fifth embodiment, wherein replacing heating provided in a conventional plant by burning a carbon-based fuel by heating provided by electricity comprises replacing one or more, most, or all feed preheaters of the chemical synthesis plant with one or more electric heaters.

A twelfth embodiment, which is the method of the fifth embodiment, wherein replacing heating provided in a conventional plant by burning a carbon-based fuel by heating provided by electricity comprises replacing one or more, most, or all reboilers of the chemical plant heated by steam or gas combustion with an electrically heated reboiler.

A thirteenth embodiment, which is the method of the fifth embodiment, wherein replacing heating provided in a conventional plant by burning a carbon-based fuel by heating provided by electricity comprises replacing one or more, most, or all distillation columns with an electrically heated distillation column.

A fourteenth embodiment, which is the method of the fifth embodiment, wherein a majority, at least 10, 20, 30, 40, 50, 60, 70, 80, 90, or substantially all of the electricity is renewable electricity from a renewable energy source.

A fifteenth embodiment, which is the method of the fifth embodiment further comprising not utilizing steam as a primary heat and/or energy transfer medium to transfer heat throughout the chemical synthesis plant.

A sixteenth embodiment, which is the method of the fifteenth embodiment, wherein not utilizing steam as a primary heat and/or energy transfer medium to transfer heat and/or energy throughout the chemical synthesis plant comprises replacing a majority, at least 10, 20, 30, 40, 50, 60, 70, 80, 90, or substantially all of the steam-turbine drives of the chemical synthesis plant with electric motors.

A seventeenth embodiment, which is the method of the fifteenth embodiment, wherein not utilizing steam as a primary heat and/or transfer medium to transfer heat throughout the chemical synthesis plant comprises replacing a majority, at least 10, 20, 30, 40, 50, 60, 70, 80, 90, or substantially all of the steam-heated reboilers of the chemical synthesis plant with electrically-heated reboilers.

An eighteenth embodiment, which is the method of the fifth embodiment, wherein the chemical synthesis plant is a steam cracking plant, an ammonia synthesis plant, or a methanol synthesis plant.

A nineteenth embodiment, which is the method of the first embodiment further comprising utilizing electrical heating of low temperature steam to further increase the energy efficiency.

A twentieth embodiment, which is the method of the first embodiment, wherein the at least one chemical product comprises propylene; ethylene oxide; monoethylene glycol; ethylene dichloride; vinyl chloride; one or more olefins; one or more diolefins; one or more isoparaffins; one or more aromatics; cyclohexane; ethylbenzene; styrene; cumene; phenol; terephthalic acid; oxygen; nitrogen; methyl tert-butyl ether (MTBE); polyethylene; polypropylene; polyvinylchloride; polystyrene; polycarbonate; polyethylene terephthalate; or a combination thereof.

A twenty-first embodiment, which is a method of operating a chemical plant, the method comprising replacing an amount of energy conventionally produced via burning of carbon-based fuel(s) by electricity, such that the greenhouse gas emissions produced by the chemical plant are reduced by greater than or equal to about 5, 10, 20, 30, 40, 50, 60, 70, 80, 90, or 100% relative to a conventional chemical plant operated with the amount of energy produced via burning of the carbon-based fuel(s).

A twenty-second embodiment, which is the method of the twenty-first embodiment, wherein the chemical plant is a steam cracking plant, an ammonia synthesis plant, or a methanol synthesis plant.

A twenty-third embodiment, which is a method of producing a chemical product, operating a chemical synthesis plant, or increasing energy efficiency during operation of a chemical synthesis plant as described herein.

Additional Disclosure Part XI

The following are non-limiting, specific embodiments in accordance with the present disclosure:

A first embodiment, which is a chemical synthesis plant comprising one or more reactors configured for producing, from one or more reactants, a process stream comprising at least one chemical product, a feed preparation system configured to prepare one or more feed streams comprising one or more of the one or more reactants for introduction into the reactor, and/or a product purification system configured to separate the at least one chemical product from reaction byproducts, unreacted reactants, or a combination thereof within the process stream, wherein the chemical synthesis plant is configured (a) such that no combustion flue gas is produced, (b) without a substantially plant-wide steam system, (c) such that no steam is utilized therein to perform mechanical work, (d) such that any steam utilized as a diluent and/or reactant within the chemical synthesis plant is generated with electricity, (e) such that any steam utilized as a diluent and/or a reactant is superheated electrically to provide heat/raise the temperature of a process stream, (f) such that heat obtained from cooling process streams is utilized solely to preheat other process streams, or (g) any combination of (a)-(f).

A second embodiment, which is the chemical synthesis plant according to the first embodiment, wherein the chemical synthesis plant does not include a flue gas heat recovery section.

A third embodiment, which is the chemical synthesis plant according to the first or the second embodiment, wherein the one or more reactors, the feed preparation system, the product purification system, or a combination thereof produces a lights stream, wherein the lights stream, the reactants, or both comprise a component selected from hydrogen, carbon monoxide, one or more light hydrocarbon, and wherein the chemical synthesis plant is not configured for combustion of the lights stream, the component, or both as a fuel, and wherein the energy of combustion is replaced by electricity.

A fourth embodiment, which is the chemical synthesis plant according to the third embodiment, wherein the chemical synthesis plant further comprises a recycle line whereby the component, the lights stream, or both can be reintroduced, either directly or following further processing and/or purification, into at least one of the one or more reactors as a reactant.

A fifth embodiment, which is the chemical synthesis plant according to the third or the fourth embodiment, wherein the component is a reactant, and wherein configuration of the chemical synthesis plant without combustion of the component provides an additional amount of the component to be converted into the at least one chemical product within the one or more reactors.

A sixth embodiment, which is the chemical synthesis plant according to any of the third through the fifth embodiments, wherein the at least one component comprises methane.

A seventh embodiment, which is the chemical synthesis plant according to any of the first through the sixth embodiments, wherein the chemical synthesis plant is configured for the production of propylene by cracking, ethylene oxide by oxidation of ethylene, monoethylene glycol by hydration of ethylene oxide, ethylene dichloride by chlorination of ethylene, vinyl chloride from ethylene dichloride, alpha-olefins by oligomerization, olefins and/or diolefins by dehydrogenation of paraffins, isoparaffins by isomerization of normal paraffins, aromatics (BTX) from paraffins and/or naphthenes by cyclization and/or dehydrogenation, aromatics from naphtha by cyclization and/or dehydrogenation, ethylbenzene by alkylation of benzene with ethylene, styrene by dehydrogenation of ethyl benzene, cumene by alkylation of benzene with propylene, phenol by oxidation of cumene, terephthalic acid by the oxidation of paraxylene, oxygen by separation from air, nitrogen by separation from air, MTBE by etherification of isobutylene, or polyethylene, polypropylene, polyvinylchloride, polystyrene, polycarbonate, or polyethylene terephthalate (PE, PP, PVC, PS, PC, PET) by polymerization.

An eighth embodiment, which is the chemical synthesis plant according to the first embodiment, wherein the chemical synthesis plant is configured for the production of acetic acid by methanol carbonylation, vinyl acetate by the reaction of acetic acid with ethylene, propylene by methanol oligomerization (generally known as the methanol-to-olefins process), aromatics by transalkylation or dealkylation, cyclohexane by hydrogenation of benzene, acrylic acid by oxidation of propylene, methacrolein by oxidation of isobutylene, methyl methacrylate by oxidation of methacrolein, acrylonitrile by ammoxidation of propylene, sulfuric acid by the oxidation of sulfur, nitric acid by the oxidation of ammonia, propylene glycol by the hydration of propylene, alcohols by hydroformylation of alkenes, esters, by condensation of carboxylic acids and alcohols, one or more nylon precursors selected from adipic acid, caprolactam, cyclohexanone, 1,6 diaminohexane, or a combination thereof, or polyvinyl alcohol (PVA), polyacrylates, polymethylmethacrylate (PMMA), nylons.

A ninth embodiment, which is the chemical synthesis plant according to any of the first through the eighth embodiments, wherein configuration of the one or more reactors, the feed preparation system, the product purification system, or a combination thereof for operation without combusting an external fuel provides for reduced carbon dioxide ($CO_2$) emissions relative to a chemical synthesis plant that is substantially the same except for being configured for operation via the combusting of the fuel.

A tenth embodiment, which is the chemical synthesis plant according to any of the first through the ninth embodiments, wherein configuration of the one or more reactors, the feed preparation system, and the product purification system for operation without combusting the fuel enables a light gas stream, a component selected from $C_1$ hydrocarbon, $C_2$ hydrocarbons, $C_3$ hydrocarbons, hydrogen, or a combination thereof to be recycled as a feed component within the chemical synthesis plant, sold, or utilized to produce another chemical in the or another chemical synthesis plant.

An eleventh embodiment, which is the chemical synthesis plant according to the tenth embodiment, further comprising a recycle line configured to recycle the light gas stream, the component selected from $C_1$ hydrocarbon, $C_2$ hydrocarbons, $C_3$ hydrocarbons, hydrogen, or a combination thereof to at least one of the one or more reactors, wherein the light gas stream, the component selected from $C_1$ hydrocarbon, $C_2$ hydrocarbons, $C_3$ hydrocarbons, hydrogen, or a combination thereof is conventionally flared or burned as a fuel.

A twelfth embodiment, which is a chemical synthesis plant for producing a chemical product, the chemical synthesis plant comprising one or more streams that are heated or cooled prior to introduction into a subsequent unit, one or more streams that are compressed prior to introduction into a subsequent unit, one or more vessels that are maintained at a predetermined operating temperature or temperature profile therealong, or a combination thereof, wherein the chemical synthesis plant is configured such that a net energy input for the heating of the one or more streams that are heated, the cooling of the one or more streams that are cooled, the compressing of the one or more streams that are compressed, and the maintaining of the one or more vessels that are maintained at the predetermined operating temperature or temperature profile can be effected without combusting a carbon-based fuel externally to the one or more vessels.

A thirteenth embodiment, which is a method of producing a chemical product, the method comprising preparing one or more feed streams comprising one or more reactants for introduction into a reactor, reacting the one or more reactants in the reactor to produce a product stream comprising the chemical product, separating the chemical product from reaction byproducts, unreacted reactants, or a combination thereof within the product stream, and/or recycling one or more of the unreacted reactants and/or reaction byproducts, wherein at least 50% of the net energy needed for powering, pumping, heating, cooling, compressing, separating, or a combination thereof utilized for one or more of the preparing, the reacting, the separating, the recycling, or a combination thereof is provided from electricity.

A fourteenth embodiment, which is the method according to the thirteenth embodiment, wherein energy for heating of the reactor is effected via a radiant section in which heat generated electrically is used to heat radiative panels which transfer heat to the reactor by radiation.

A fifteenth embodiment, which is the method according to the thirteenth embodiment, wherein energy for one or more feed preheaters of the chemical synthesis plant is provided by electric heaters.

A sixteenth embodiment, which is the method according to the thirteenth embodiment, further comprising utilizing electrical heating of low temperature steam to further increase energy efficiency.

While preferred embodiments of the invention have been shown and described, modifications thereof can be made by one skilled in the art without departing from the teachings of this disclosure. The embodiments described herein are exemplary only, and are not intended to be limiting. Many variations and modifications of the invention disclosed herein are possible and are within the scope of the invention.

Numerous other modifications, equivalents, and alternatives, will become apparent to those skilled in the art once the above disclosure is fully appreciated. It is intended that the following claims be interpreted to embrace all such modifications, equivalents, and alternatives where applicable. Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

What is claimed is:

1. A chemical synthesis plant comprising:
   one or more electrified reactors each configured for producing, from one or more reactants, a process stream comprising at least one chemical product;
   an electrified feed preparation system configured to prepare one or more feed streams comprising one or more of the one or more reactants for introduction into the one or more electrified reactors; and
   a product purification system configured to separate the at least one chemical product from reaction byproducts, unreacted reactants, or a combination thereof within the process stream,
   wherein the chemical synthesis plant is configured:
   (a) such that any steam utilized as a diluent and/or reactant within the chemical synthesis plant is generated with electricity;
   (b) such that any steam utilized as a diluent and/or a reactant is superheated electrically to provide heat/raise the temperature of a process stream;
   (c) such that heat obtained from cooling process streams is utilized solely to preheat other process streams; or
   (d) any combination of (a)-(c);
   wherein the electrified feed preparation system and the one or more electrified reactors are configured such that greater than 90% of the net energy needed for heating, cooling, compressing, or a combination thereof is provided by electricity; and
   wherein the at least one chemical product comprises a chemical product produced by a method selected from the list of chemical products and corresponding production methods consisting of:
   propylene by cracking;
   ethylene oxide by oxidation of ethylene;
   monoethylene glycol by hydration of ethylene oxide;
   ethylene dichloride by chlorination of ethylene;
   vinyl chloride from ethylene dichloride;
   alpha-olefins by oligomerization;
   olefins and/or diolefins by dehydrogenation of paraffins;
   isoparaffins by isomerization of normal paraffins;
   aromatics (BTX) from paraffins and/or naphthenes by cyclization and/or dehydrogenation;
   aromatics from naphtha by cyclization and/or dehydrogenation;
   ethylbenzene by alkylation of benzene with ethylene;
   styrene by dehydrogenation of ethyl benzene;
   cumene by alkylation of benzene with propylene;
   phenol by oxidation of cumene;
   terephthalic acid by the oxidation of paraxylene;
   oxygen by separation from air;
   nitrogen by separation from air;
   MTBE by etherification of isobutylene; or
   polyethylene, polypropylene, polyvinylchloride, polystyrene, polycarbonate, and
   polyethylene terephthalate (PE, PP, PVC, PS, PC, PET) by polymerization.

2. The chemical synthesis plant according to claim 1, wherein the chemical synthesis plant does not include a flue gas heat recovery section.

3. The chemical synthesis plant according to claim 1, wherein at least one of the one or more electrified reactors, the feed preparation system, the product purification system, or a combination thereof is configured to produce a lights stream, wherein the lights stream comprises a component selected from the list of components consisting of: hydrogen, carbon monoxide, one or more light hydrocarbons; and
   wherein the chemical synthesis plant is configured to not combust the component; and
   wherein the chemical synthesis plant is configured to use electricity for energy that could otherwise be provided by combustion of the component; and
   wherein, when the component includes one or more light hydrocarbons, the one or more light hydrocarbons comprise a $C_1$ hydrocarbon, a $C_2$ hydrocarbon, $C_3$ hydrocarbon, and/or a $C_4$ hydrocarbon.

4. The chemical synthesis plant according to claim 3, further comprising:
   a recycle line whereby the component, the lights stream, or both can be reintroduced, either directly or following further processing and/or purification, into at least one of the one or more reactors as a reactant.

5. The chemical synthesis plant according to claim 3, wherein the chemical synthesis plant is configured to use the component as a reactant, and wherein the chemical synthesis plant is configured to not combust the component such that the component is available to be converted into the at least one chemical product within the one or more reactors.

6. The chemical synthesis plant according to claim 3, wherein the chemical synthesis plant is configured such that the component comprises methane.

7. The chemical synthesis plant according to claim 1, wherein the one or more electrified reactors, the electrified feed preparation system, the product purification system, or a combination thereof is configured to operate without combusting an external fuel, such that operation of the chemical synthesis plant generates reduced carbon dioxide ($CO_2$) emissions relative to operation of a reference chemical synthesis plant that is substantially the same except for combusting a fuel for energy.

8. The chemical synthesis plant according to claim 1, wherein the one or more electrified reactors, the feed preparation system, and the product purification system for operation are configured to not combust a component of a light gas stream and the plant is configured to direct the component to at least one purpose selected from the list of purposes consisting of: recycled as a feed component within the chemical synthesis plant, sold, utilized to produce another chemical in the or another chemical synthesis plant, and combinations thereof.

9. The chemical synthesis plant according to claim 8, further comprising:
a recycle line configured to recycle the component of the light gas stream to at least one of the one or more electrified reactors as a reactant;
wherein the component of the light gas stream is selected from the list of components consisting of: $C_1$ hydrocarbon, $C_2$ hydrocarbons, $C_3$ hydrocarbons, hydrogen, and combinations thereof.

10. The chemical synthesis plant of claim 1, wherein the chemical synthesis plant is configured to operate such that no combustion flue gas is produced.

11. The chemical synthesis plant of claim 1, wherein the chemical synthesis plant is configured without a substantially plant-wide steam system.

12. The chemical synthesis plant of claim 1, wherein the chemical synthesis plant is configured such that no steam is utilized in the chemical synthesis plant to perform mechanical work.

13. The chemical synthesis plant of claim 1, wherein the chemical synthesis plant is configured such that any steam utilized as a diluent and/or reactant within the chemical synthesis plant is generated with electricity.

14. The chemical synthesis plant of claim 1, wherein the chemical synthesis plant is configured such that any steam utilized as a diluent and/or a reactant is superheated electrically to provide heat/raise the temperature of a process stream.

15. The chemical synthesis plant of claim 1, wherein the chemical synthesis plant is configured such that heat obtained from cooling process streams is utilized solely to preheat other process streams.

16. The chemical synthesis plant of claim 1, wherein the product purification system is electrified and wherein a majority of the net energy needed for the separating is provided by the electricity.

17. The chemical synthesis plant of claim 16, wherein the product purification system is electrified, and
wherein greater than 90% of the net energy needed for the separating is provided by electricity.

18. The chemical synthesis plant of claim 1, wherein the chemical synthesis plant is configured such that at least one of the one or more reactants comprises a component selected from hydrogen, carbon monoxide, a $C_2$-$C_4$ hydrocarbon, or a combination thereof.

19. The chemical synthesis plant of claim 1, wherein the one or more electrified reactors are configured for a steam-free process or a substantially steam free for the producing, from the one or more reactants, the product stream.

20. The chemical synthesis plant of claim 1, wherein all the chemical synthesis plant is configured such that all electricity used by the chemical synthesis plant is produced from a non-carbon based energy source.

21. The chemical synthesis plant of claim 1, wherein the chemical synthesis plant is configured such that at least one of the one or more reactants comprises a component selected from the list of components consisting of: hydrogen, carbon monoxide, a $C_2$-$C_4$ hydrocarbon, and combinations thereof.

* * * * *